(12) United States Patent
Ishizawa et al.

(10) Patent No.: US 10,376,160 B2
(45) Date of Patent: Aug. 13, 2019

(54) BLOOD PRESSURE ESTIMATION METHOD AND BLOOD PRESSURE MEASUREMENT DEVICE

(71) Applicant: SHINSHU UNIVERSITY, Matsumoto-shi, Nagano (JP)

(72) Inventors: Hiroaki Ishizawa, Ueda (JP); Shouhei Koyama, Ueda (JP)

(73) Assignee: SHINSHU UNIVERSITY, Matsumoto-Shi, Nagano (JP)

( * ) Notice: Subject to any disclaimer, the term of this patent is extended or adjusted under 35 U.S.C. 154(b) by 244 days.

(21) Appl. No.: 15/309,569

(22) PCT Filed: May 14, 2015

(86) PCT No.: PCT/JP2015/063928
§ 371 (c)(1),
(2) Date: Nov. 8, 2016

(87) PCT Pub. No.: WO2015/174499
PCT Pub. Date: Nov. 19, 2015

(65) Prior Publication Data
US 2017/0135591 A1    May 18, 2017

(30) Foreign Application Priority Data

May 14, 2014   (JP) ................................ 2014-100284
Mar. 6, 2015   (JP) ................................ 2015-044261

(51) Int. Cl.
*A61B 5/021*   (2006.01)
*A61B 5/00*    (2006.01)

(52) U.S. Cl.
CPC ........ *A61B 5/02108* (2013.01); *A61B 5/0075* (2013.01); *A61B 5/7235* (2013.01);
(Continued)

(58) Field of Classification Search
CPC .................................................. A61B 5/02108
See application file for complete search history.

(56) References Cited

U.S. PATENT DOCUMENTS

2011/0009755 A1*   1/2011   Wenzel ............... A61B 5/0215
                                                        600/485

FOREIGN PATENT DOCUMENTS

JP   10-248818 A      9/1998
JP   10248818 A   *  9/1998
(Continued)

OTHER PUBLICATIONS

Witt et al. "Fiber optic heart rate sensor for integration into personal protective equipment." IEEE. Jul. 22, 2011. (Year: 2011).*
(Continued)

*Primary Examiner* — Meredith Weare
(74) *Attorney, Agent, or Firm* — Flynn Thiel, P.C.

(57) ABSTRACT

A blood pressure measurement method uses a pulse wave measurement unit (20) for measuring the pulse wave of a subject using an FBG sensor (10), and a blood pressure value calculation unit (30) for calculating a blood pressure value from waveform date of the measured pulse wave. The blood pressure calculation unit (30) uses a calibration model representing the correlation between measured waveform date of a previously measured pulse wave, and a measured blood pressure value measured by an automatic blood pressure gauge at each measurement point in time of the measured waveform date to estimate the blood pressure value of the subject from the measured waveform date of the pulse wave. It is possible to realize an easy-to-use blood pressure measurement method capable of estimating the blood pressure value with accuracy required for the automatic blood pressure gauge and continuously measuring the blood pressure.

3 Claims, 35 Drawing Sheets

(52) U.S. Cl.
CPC ..... *A61B 5/7264* (2013.01); *A61B 2560/0223* (2013.01); *A61B 2562/0266* (2013.01)

(56) References Cited

FOREIGN PATENT DOCUMENTS

| | | |
|---|---|---|
| JP | 10-295656 A | 11/1998 |
| JP | 2002-320593 A | 11/2002 |
| JP | 2003-515104 A | 4/2003 |
| WO | WO 2013/180085 A1 | 12/2013 |

OTHER PUBLICATIONS

Dziuda et al. "Fiber Bragg grating-based sensor for monitoring respiration and heart activity during magnetic resonance imaging examinations" (Abstract). J Biomed Opt. May 2013;18(5):57006. (Year: 2013).*

Leitao et al. "Feasibility studies of Bragg probe for noninvasive carotid pulse waveform assessment" (Abstract). J Biomed Opt. Jan. 2013;18(1):17006. (Year: 2013).*

International Search Report from PCT/2015/063928 (2 pgs.).

Cuffless Blood Pressure Estimation based on Photoplethysmograph Signal by Classifying on account of Cardiovascular Characteristics, by S. Suzuki et al, IEICE Technical Report, Dec. 2008, vol. 108, No. 371, pp. 1-4.

A reconstruction of acceleration plethysmograph with aging by utilizing a cardiovascular model, by T. Kaminuma et al, IEICE Technical Report, Mar. 1999, vol. 98, No. 672, pp. 107-114.

* cited by examiner

SUBJECT A

SUBJECT B

SUBJECT C

BLOOD PRESSURE ESTIMATION METHOD AND BLOOD PRESSURE MEASUREMENT DEVICE

TECHNICAL FIELD

The present invention relates to a blood pressure estimation method of using an acceleration pulse wave measured from a subject to estimate a blood pressure value of the subject, and to a blood pressure measurement device that uses this blood pressure estimation method.

BACKGROUND ART

Blood pressure is often measured as biological information indicating a person's state of health. One proposed method of measuring blood pressure is a method of measuring the pulse wave of a subject and calculating blood pressure on the basis of the measured pulse wave. In Patent Document 1, the applicant proposed a noninvasive blood pressure measurement method for estimating the blood pressure of a subject from the time difference (propagation velocity) between pulse waves measured by fiber Bragg grating sensors (referred to below as "FBG sensors") attached to multiple locations on the subject.

Patent Document 2 proposes a method of detecting a parameter such as the time taken by an arterial waveform to reach a maximum value from a minimum value, on the basis of the arterial waveform, and detecting a highest blood pressure and a lowest blood pressure. Patent Document 3 proposes a method of calculating an acceleration pulse wave from a measured volume pulse wave, and determining the highest blood pressure and lowest blood pressure of the subject from the inflection point of the acceleration pulse wave.

PRIOR ART DOCUMENTS

Patent Documents

Patent Document 1: WO 2013/180085
Patent Document 2: JP-A 2002-320593
Patent Document 3: JP-A 10-295656

SUMMARY OF THE INVENTION

Problems to be Solved by the Invention

The method disclosed in Patent Document 1, in which blood pressure is estimated from the propagation velocity of the pulse wave of the subject, must use multiple FBG sensors in order to detect the pulse wave. The methods disclosed in Patent Documents 2 and 3, in which blood pressure is estimated on the basis of the characteristics of the pulse wave waveform and the pulse wave pattern, requires calculation of the zero cross point of the waveform and computations such as differential processing of the waveform, and blood pressure cannot always be estimated accurately.

An object of the present invention is to provide a blood pressure estimation method whereby blood pressure can be estimated simply and with high accuracy on the basis of an acceleration pulse wave measured from a subject, and a blood pressure measurement device that uses this blood pressure estimation method.

Means of Solving the Problems

The blood pressure estimation method of the present invention is characterized in that there is constructed a calibration model that represents the correlation between measured waveform data of a measured acceleration pulse wave and measured blood pressure values measured at individual measurement time points of the measured waveform data, and the calibration model is used to estimate blood pressure values of a subject at the time of the acceleration pulse wave measurement, from the waveform data of the acceleration pulse wave measured from the subject.

With the method of the present invention, a calibration model constructed in advance is used to estimate blood pressure values of the subject at the time of pulse wave measurement from the waveform data of the acceleration pulse wave of the subject. According to verification tests done by the inventors, it was confirmed that the international standard, which is that the average range be within 5 mmg as the target accuracy of prediction, is met by appropriately constructing a calibration model.

Blood pressure values include systolic blood pressure (maximum blood pressure) and diastolic blood pressure (minimum blood pressure). To estimate these types of blood pressure from the waveform data of the acceleration pulse wave, a first calibration model representing the correlation between pulse wave waveform data and systolic blood pressure values, and a second calibration model representing the correlation between pulse wave waveform data and diastolic blood pressure values, are preferably constructed as the calibration model.

The calibration model used in the method of the present invention can be calculated by extracting one-cycle waveform data from the measured waveform data, standardizing each set of the extracted one-cycle waveform data either so that the amount of wavelength displacement is the same or so that the amount of wavelength displacement and the time span are the same, and performing regression analysis with the standardized one-cycle waveform data as an explanatory variable and the measured blood pressure value as an objective variable.

The calibration model is preferably calculated using the PLS (partial least squares) regression analysis method.

Next, the blood pressure measurement device of the present invention is characterized by having:
a pulse wave measurement unit for measuring an acceleration pulse wave of a subject; and
a blood pressure value calculation unit for using a calibration model representing a correlation between measured waveform data of an acceleration pulse wave measured in advance, and measured blood pressure values measured at individual measurement time points of the measured waveform data, to estimate a blood pressure value of the subject at the time of the acceleration pulse wave measurement from waveform data of the acceleration pulse wave measured by the pulse wave measurement unit.

A versatile calibration model that has been constructed in advance can be used as the calibration model. Alternatively, at times such as before measurement is started, a calibration model can be constructed from the waveform data of numerous acceleration pulse waves and numerous measured blood pressure values, and the calibration model, which represent the correlation between the waveform data and the blood pressure values, can be used to approximate actual blood pressure measurements. The calibration model is reconstructed in cases such as when, e.g., calibration is performed periodically.

In this case, the blood pressure measurement device of the present invention has a calibration model construction unit that uses a predetermined number of the measured waveform data sets and a predetermined number of the measured blood pressure values measured at each measurement time point of the measured waveform data to construct the calibration model.

Moreover, the calibration model can be calculated by extracting one-cycle waveform data from the measured waveform data, and performing regression analysis with the extracted one-cycle waveform data as an explanatory variable and the measured blood pressure value as an objective variable.

In this case, to increase the accuracy of predicting blood pressure values, the calibration model is preferably calculated by standardizing each set of the extracted one-cycle waveform data either so that the amount of wavelength displacement is the same or so that the amount of wavelength displacement and the time span are the same, and using the standardized one-cycle waveform data as the explanatory variables.

A method of evening up the lengths of each set of one-cycle waveform data to the minimum time span of these one-cycle waveform data sets can be used as the method of standardization for making the time span the same.

Various methods could be used as the regression analysis method for constructing the calibration model, but the PLS regression analysis method is preferably used.

The blood pressure value calculation unit may estimate a systolic blood pressure value and/or a diastolic blood pressure value of the subject.

In the present invention, the pulse wave measurement unit preferably has a sensor provided with the required accuracy as the sensor that acquires the acceleration pulse wave. Particularly, an FBG sensor that measures the acceleration pulse wave is preferably provided as the sensor. Using this sensor makes it possible to measure the acceleration pulse wave with precision, and the accuracy of measuring (accuracy of estimating) blood pressure values can therefore be increased.

Instead of directly detecting the acceleration pulse wave, a sensor for measuring volume pulse waves can be arranged, and the measured volume pulse waves can be subjected to secondary differentiation to calculate the acceleration pulse wave.

Effects of the Invention

The inventors conducted tests to verify the calibration model, primarily with respect to the following items, as is described hereinafter.

(a) Effects from individual differences on blood pressure value estimation accuracy (b) Relationship between measured position of acceleration pulse wave and blood pressure value estimation accuracy (c) Estimation accuracy for systolic blood pressure and diastolic blood pressure (d) Relationship between standardization of measured waveform data of acceleration pulse wave and blood pressure value estimation accuracy (e) Relationship between factor number in PLS regression analysis and blood pressure value estimation accuracy As a result of the verification tests pertaining to these matters, it was confirmed that using the blood pressure estimation method of the present invention made it possible to estimate blood pressure values with predetermined estimation accuracy, regardless of individual differences, differences in the measured positions of pulse waves, and differences between systolic blood pressure and diastolic blood pressure. Consequently, with the blood pressure measurement device of the present invention, it is possible to calculate blood pressure values from acceleration pulse waves with at least the same degree of accuracy as a conventional blood pressure gauge. Therefore, it is possible to achieve a blood pressure measurement device in which blood pressure values are accurately obtained with a simple configuration.

In the blood pressure estimation method of the present invention, it was confirmed that by appropriately standardizing waveform data of acceleration pulse waves obtained through measurement, a calibration model of high estimation accuracy can be constructed, and when PLS regression analysis is used, a calibration model of high estimation accuracy can be constructed by appropriately setting the factor number of the analysis. Consequently, with the blood pressure measurement device of the present invention, blood pressure values can be calculated with high accuracy from acceleration pulse waves by appropriately standardizing waveform data and setting an appropriate factor number in the PLS regression analysis.

Furthermore, with the blood pressure measurement device of the present invention, blood pressure values can be ascertained merely by attaching a pulse wave detection sensor to a location where pulse waves are easily detected, such as the elbow or wrist of the subject, and detecting pulse waves. The sensor need only be attached to one location. In cases such as when blood pressure is continuously measured, measurement can continue while body posture changes, and continuous blood pressure measurement can be performed with minimal stress imposed on the subject. Consequently, an easy-to-use blood pressure measurement device can be achieved. Furthermore, by making the processing of pulse wave waveform data into an automatic program, the calibration model construction can be performed in a simple manner, as can the blood pressure measurement based on the calibration model, and the device is easily reduced in size.

MODE FOR CARRYING OUT THE INVENTION

Blood Pressure Measurement Device

Figure 1A:
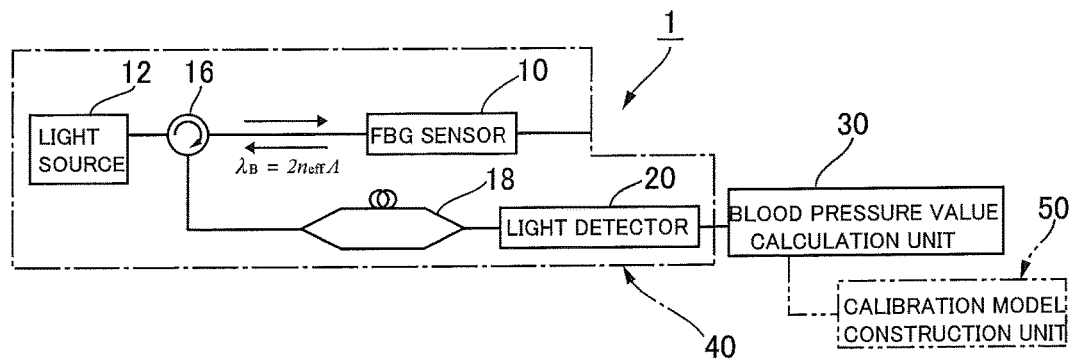
FIG. 1 is a block diagram showing a configuration example of the blood pressure measurement device, and a summary flowchart showing the blood pressure estimation method.
Figure 1B:
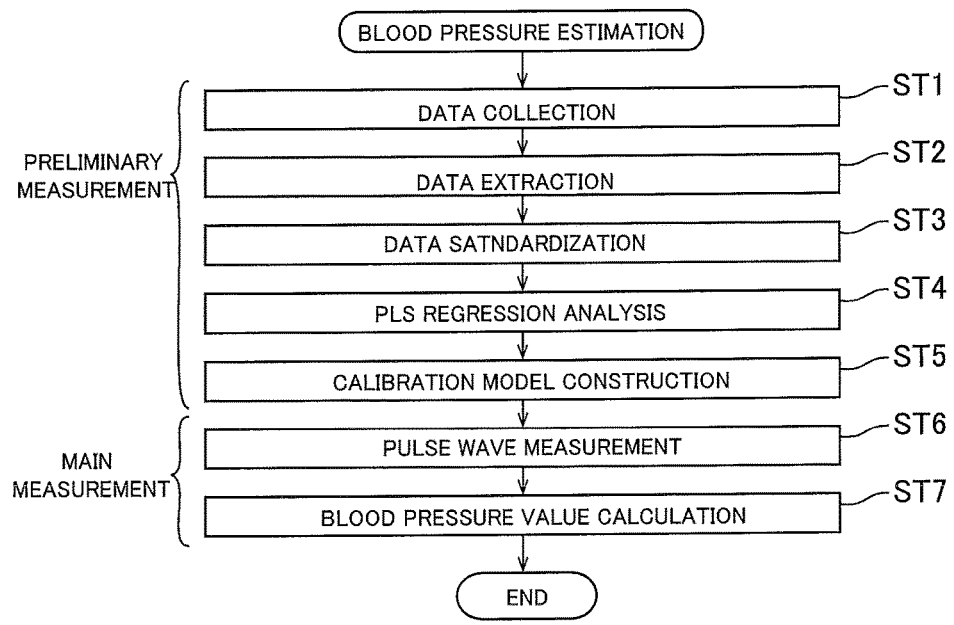

FIG. 1(*a*) is a block diagram showing a configuration example of a blood pressure measurement device to which the present invention is applied. A blood pressure measurement device 1 is provided with: an FBG sensor 10 attached to a location where the pulse wave of the subject is measured, e.g., a location where the pulse wave is easily measured such as the inside of the wrist or the inside of the elbow; a light source 12 for reference, shone onto the FBG sensor 10; a light detector 20 for detecting light reflected from the FBG sensor 10, and a blood pressure value calculation unit 30 for calculating a blood pressure value on the basis of the detection result of the light detector 20. Disposed on the blood pressure value calculation unit 30, as necessary, are a recording unit for recording the blood pressure value of the subject, a display unit for displaying the blood pressure value, and an operating unit provided with switches and the like for performing various control operations.

In the FBG sensor 10, diffraction grating structures are formed at predetermined intervals within one optical fiber. In a test described hereinafter, the sensor used as the FBG sensor 10 had a sensor section length of 10 mm, a wavelength resolution of ±0.1 pm, and a wavelength range of 1550±0.5 nm. The fiber diameter was 145 μm and the core diameter was 10.5 um. In this test, the wrist and elbow were the measurement locations, and the FBG sensor 10 was attached to these measurement locations by medical tape. In cases where there is a risk of the FBG sensor 10 becoming positionally misaligned at the attached position, the FBG sensor 10 is preferably brought in contact with the skin, and attached by being wound with a bandage with the aid of a cushioning such as a sponge.

An amplified spontaneous emission (ASE) light source having a wavelength range of 1525 to 1570 nm was used for the light source 12. Outgoing light from the light source 12 is shone onto the FBG sensor 10 via a circulator 16. Reflected light from the FBG sensor 10 is guided to a Mach-Zehnder interferometer 18 via the circulator 16, and output light from the Mach-Zehnder interferometer 18 is detected by the light detector 20.

The Mach-Zehnder interferometer 18 is for dividing the light, using a beam splitter, into two optical paths having an optical path difference, and superposing the optical paths together through a beam splitter to produce interference light. To create an optical path difference, one optical fiber is lengthened in the present example. In coherent light, an interference fringe occurs in accordance with the optical path difference, and changes in distortion occurring in the FBG sensor 10, i.e., acceleration pulse waves can therefore be detected by measuring the pattern of the interference fringe.

In the blood pressure measurement device 1, the section that detects the amount of distortion in the FBG sensor 10 to detect the waveform of the acceleration pulse wave is a pulse wave measurement unit 40. The pulse wave measurement unit 40 includes: an optical system containing components such as the light source 12, the circulator 16, the Mach-Zehnder interferometer 18, and a beam splitter; the light detector 20; and analyzing means or the like, included in the light detector 20, for analyzing the amount of wavelength shift.

The pulse wave measurement unit 40 can be used with different selections of light sources and bands of light, in accordance with the characteristics of the FBG sensor 10 being used. Various methods can also be employed for the analyzing means for the wave detection method or the like.

The blood pressure value calculation unit 30 is provided with a function for detecting waveform data of the acceleration pulse wave on the basis of the result of the light detector 20 detecting the optic signal from the FBG sensor 10, and predicting (estimating) a blood pressure value on the basis of the detected waveform data. As will be described hereinafter, a correlation between waveform data of the acceleration pulse wave and blood pressure values can be found by performing specific data processing. Therefore, the blood pressure of the subject can be continuously measured by utilizing the blood pressure measurement device 1 shown in FIG. 1.

FIG. 1(*b*) is a summary flowchart showing the blood pressure estimation method employed in the blood pressure measurement device 1. First, in preliminary measurement (steps ST1 to ST5), the acceleration pulse wave and blood pressure value are simultaneously measured as many times as is needed, and a calibration model is constructed, which represents the correlation between measured waveform data of the measured acceleration pulse waves, and measured blood pressure values measured at each measurement point in time of the measured waveform data. In main measurement (steps ST6 and ST7), during which the actual blood pressure measurement is performed, the acceleration pulse wave of the subject is measured using the FBG sensor 10, and the blood pressure value calculation unit 30 uses the calibration model to predict (estimate) the blood pressure value of the subject at the time of acceleration pulse wave measurement from the obtained waveform data.

Both a first calibration model representing the correlation between measured waveform data and systolic blood pressure values which are measured blood pressure values, and a second calibration model representing the correlation between measured waveform data and diastolic blood pressure values, which are measured blood pressure values, can be constructed as calibration models. Another option is to construct one of these models and to measure either only systolic blood pressure values or only diastolic blood pressure values.

Calibration model construction is specifically performed with the following procedure. First, in preliminary measurement, the acceleration pulse wave is measured and blood pressure is measured by an automatic blood pressure gauge at the time of each acceleration pulse wave measurement, and the required amount of acceleration pulse wave data and corresponding blood pressure value data are collected (step ST1: data collection). Data can be collected from the same person or from multiple people.

For each of a plurality of collected acceleration pulse waves, data for each cycle, equivalent to one pulse beat in a point in time corresponding to the blood pressure measurement time point, is extracted from the waveform data of the pulse wave, and this data is used as one-cycle waveform data of each acceleration pulse wave (step ST2: data extraction).

Next, a process is performed to standardize the one-cycle waveform data of each of the plurality of acceleration pulse waves (step ST3: data standardization). The standardization process involves the use of a wavelength displacement standardization process of standardizing data so that the amount of wavelength displacement is constant, and a time span standardization process of standardizing data so that the time span is constant. As is described hereinafter, it is preferable to perform the wavelength displacement standardization process, or to perform both the wavelength displacement standardization process and the time span standardization process.

Using multiple sets of standardized one-cycle waveform data as explanatory variables and measured blood pressure values corresponding to each set of one-cycle waveform data as objective variables, a regression analysis is performed and a calibration model is constructed (step ST4: PLS regression analysis, step ST5: calibration model construction). A PSL regression analysis method can be used as the regression analysis method.

The blood pressure measurement device 1 in this embodiment may be provided with a calibration model construction unit 50 for constructing a calibration model from waveform data of acceleration pulse waves and actual measured values of blood pressure, as is shown by the imaginary lines in FIG. 1(a). The calibration model construction unit 50 can be used to reconstruct or correct the calibration model as necessary.

As a result of conducting tests using the blood pressure measurement device 1 employing the blood pressure estimation method according to the present invention, the inventors have discovered that blood pressure values can be estimated (predicted) with sufficiently high accuracy and the blood pressure measurement device according to the present invention is sufficiently practical. Three types of tests, from among the tests conducted by the inventors, are described below as Test Examples 1, 2, and 3.

Test Examples 1 to 3 demonstrate that a blood pressure value can be estimated from a measured pulse wave, using a calibration model constructed on the basis of the correlation between a pulse wave waveform and an actual measured blood pressure value. Test Example 2 demonstrates that a blood pressure value can be estimated using a calibration model shared among different subjects. Test Example 3 demonstrates that both systolic blood pressure and diastolic blood pressure can be estimated as blood pressure values through the estimation method of the present invention.

Test Example 1

A test and an analysis were conducted with the following procedure in order to examine the correlation between a subject's acceleration pulse wave and blood pressure value, or systolic blood pressure in the present example.

To detect the pulse wave using an FBG sensor, FBG sensors were attached to the location of an artery on the inside of the writs and to the location of an artery on the inside of the elbow, and the pulse waves of the wrist and elbow were detected. To observe the correlation between the waveform data of the detected pulse waves and blood pressure values, when pulse wave waveform data was detected using the FBG sensors, an automatic blood pressure gauge (electronic blood pressure gauge: HEM-120 made by Omron corporation) was simultaneously used to monitor blood pressure values of the subject. Tests were performed separately for the wrist pulse wave and the elbow pulse wave. Measurement was conducted with the subject lying supine, one measurement time span for acquiring data was 15 seconds, and the sampling frequency was 10 kHz.

The waveforms of pulse waves obtained using FBG sensors are acceleration pulse waves, equivalent to second derivatives of volume pulse waves. Specifically, one-cycle waveform data extracted between peak positions of a pulse wave is equivalent to one pulse of a volume pulse wave. In the following description, the acceleration pulse wave detected using an FBG sensor is sometimes referred to simply as the "pulse wave."

Figure 2:
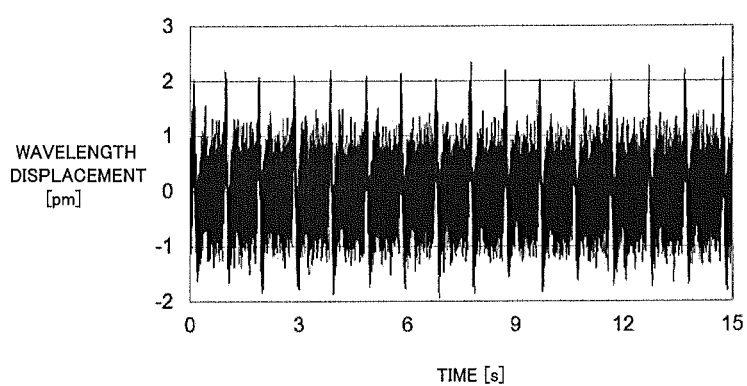
FIG. 2 is a waveform graph showing measured waveform data of a pulse wave acquired using an FBG sensor.

FIG. 2 is an example of a pulse wave waveform detected using the blood pressure measurement device 1 shown in FIG. 1. The change in distortion occurring in the FBG sensor in correspondence with pulsation is captured as a cyclic pulse wave. To analyze the correlation between the waveform data of the acquired pulse wave and the blood pressure value (systolic blood pressure), in the present test, the PLS regression analysis method was utilized to analyze the correlation, with an explanatory variable used as waveform data of the pulse wave acquired by the FBG sensor, and an objective variable used as systolic blood pressure measured by the automatic blood pressure gauge.

Because the blood pressure value measurement using an automatic blood pressure gauge is not a continuous measurement, one set of waveform data of the pulse wave of the FBG sensor corresponding to the time point of the reference blood pressure measurement, i.e., one-cycle waveform data is used as the explanatory variable. The exact measurement time point is unknown because blood pressure measurement using an automatic blood pressure gauge is not continuous measurement, and an automatic blood pressure gauge takes measurement using a cuff. In view of this, one-cycle waveform data of the immediate pulse wave at the time of the reference blood pressure measurement was selected as the explanatory variable. In effect, it is possible that the measurement time point for the reference blood pressure and the measurement time point for the one-cycle waveform data, selected as the explanatory variable and obtained from the FBG sensor, will not strictly coincide.

The PLS regression analysis method is an analysis technique that presumes there will be an error in the reference blood pressure value obtained by the automatic blood pressure gauge as the reference value, and sequentially reduces the error in the reference value as the objective variable. Consequently, this method is effective for analyzing the correlation between pulse wave waveform data and blood pressure values.

Figure 3:
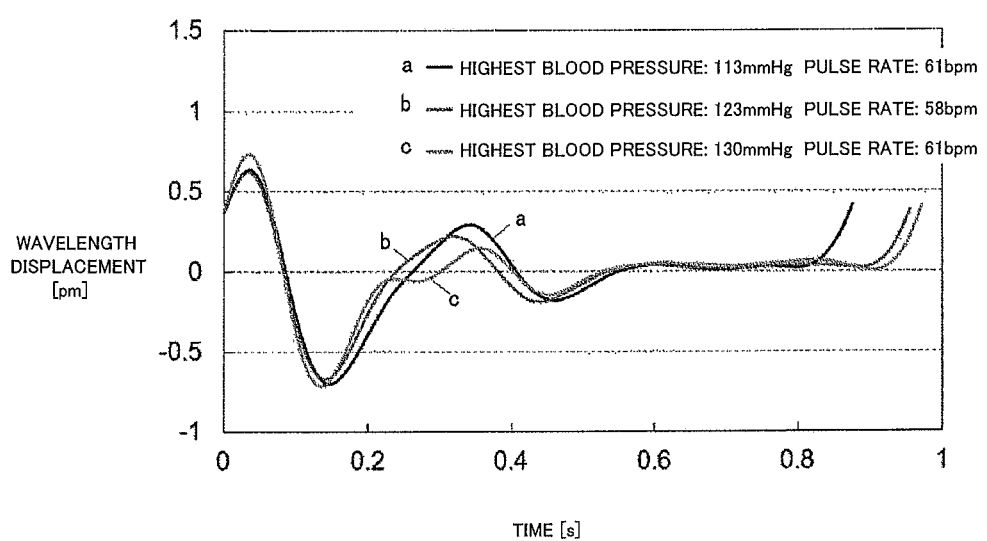
FIG. 3 is a waveform graph showing one-cycle waveform data extracted from measured waveform data.

FIG. 3 is a waveform graph showing one-cycle waveform data extracted from measured waveform data obtained by the FBG sensor when the highest blood pressure value (systolic blood pressure) is 113 mmHg, 123 mmHg, and 130 mmHg. These sets of waveform data are extracted as pulse wave waveform data at the measurement time point corresponding to the reference blood pressure, which was measured using an automatic blood pressure gauge.

Observing the one-cycle waveform data of FIG. 3, it is clear that the time of one pulse wave cycle differs when the blood pressure value differs. In view of this, to harmonize the cycle time of each one-cycle waveform data to be processed, a process (time span standardization process) was performed, within the time span of one-cycle waveform data having the shortest cycle from among all data being analyzed, to extract a pulse wave waveform to be analyzed.

Figure 4:
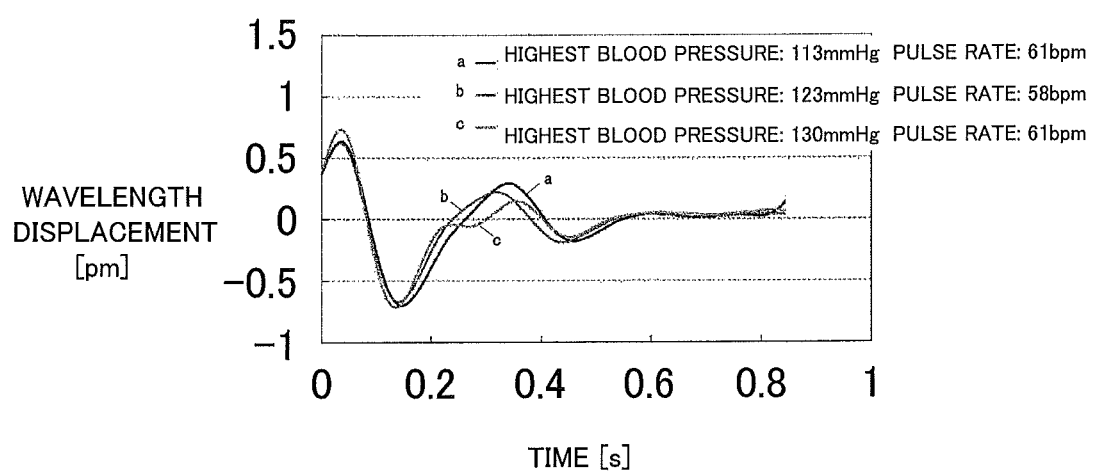
FIG. 4 is a waveform graph showing one-cycle waveform data that has undergone a time span standardization process.

FIG. 4 is a waveform graph showing one-cycle waveform data obtained by performing the time span standardization process on the waveform data shown in FIG. 3. Through this process, data at the final end of each set of one-cycle waveform data is cut and the time spans of all sets of one-cycle waveform data are harmonized. Analysis involves performing the time span standardization process on all sets of one-cycle waveform data to be analyzed. Because there is a large difference among the waveform data sets at the final end of the one-cycle waveform data (the rising portions at the right ends of the waveforms of FIG. 3) as shown in FIG. 3, the purpose of performing the time span standardization process is to remove these portions and make the main portion of each one-cycle waveform data (the range preceding the 0.8 second mark) the portion to be analyzed.

Observing the amount of wavelength displacement on the vertical axis for the waveform data that has undergone the time span standardization process shown in FIG. 4, it is clear that the amount of displacement differs according to the blood pressure value. The amount of wavelength displacement is equivalent to the size of distortion in the FBG sensor, and when the blood pressure differs, the size of the distortion in the FBG sensor is also shown to differ.

Figure 5:
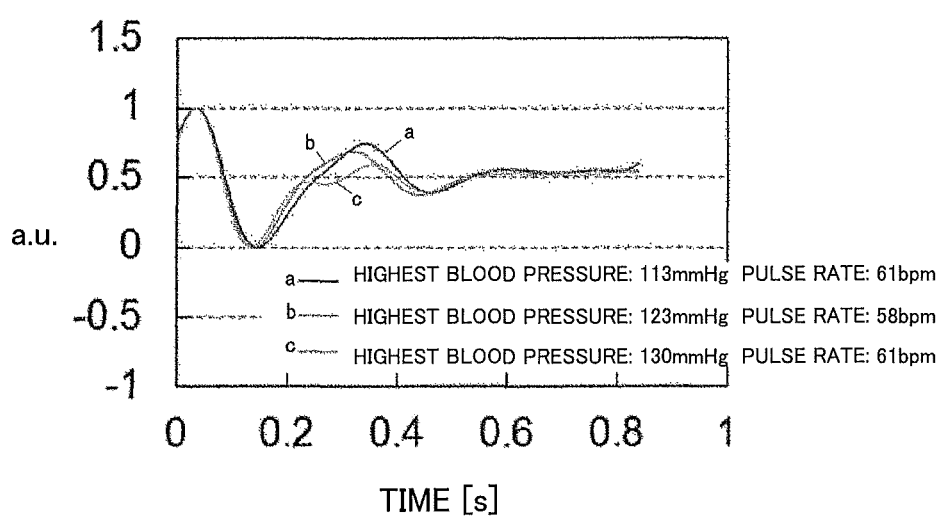
FIG. 5 is a waveform graph showing one-cycle waveform data that has undergone a time span standardization process and a wavelength displacement standardization process.

FIG. 5 is a waveform graph showing one-cycle waveform data obtained by performing the wavelength displacement standardization process yet again on the one-cycle waveform data that has undergone the time span standardization process shown in FIG. 4. In the wavelength displacement standardization process of the present test example, the standardization process was performed so that the minimum wavelength displacement value was 0 and the maximum wavelength displacement value was 1. The conditions for standardizing the amount of wavelength displacement can be appropriately set so that, e.g., the minimum value is −1 and the maximum value is +1.

(Analysis Results)

To construct the calibration model in the present test, analysis was performed for both a case in which the process of standardizing the amount of wavelength displacement was not performed, and a case in which standardization was performed on the amount of wavelength displacement.

Figure 6:
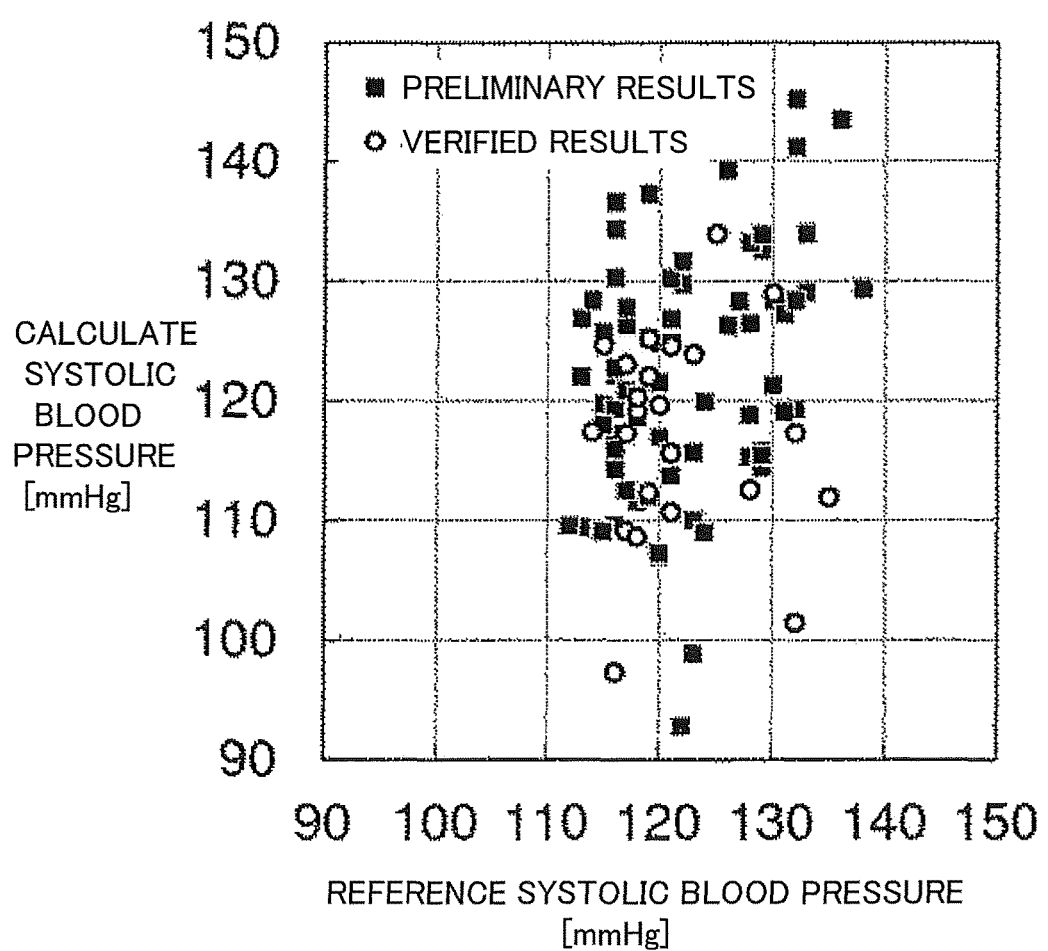
FIG. 6 is a correlation chart showing the correlation between calculated systolic blood pressure, which is estimated from waveform data obtained from performing the time span standardization process on a pulse wave measured at the elbow, and reference systolic blood pressure.
Figure 7:
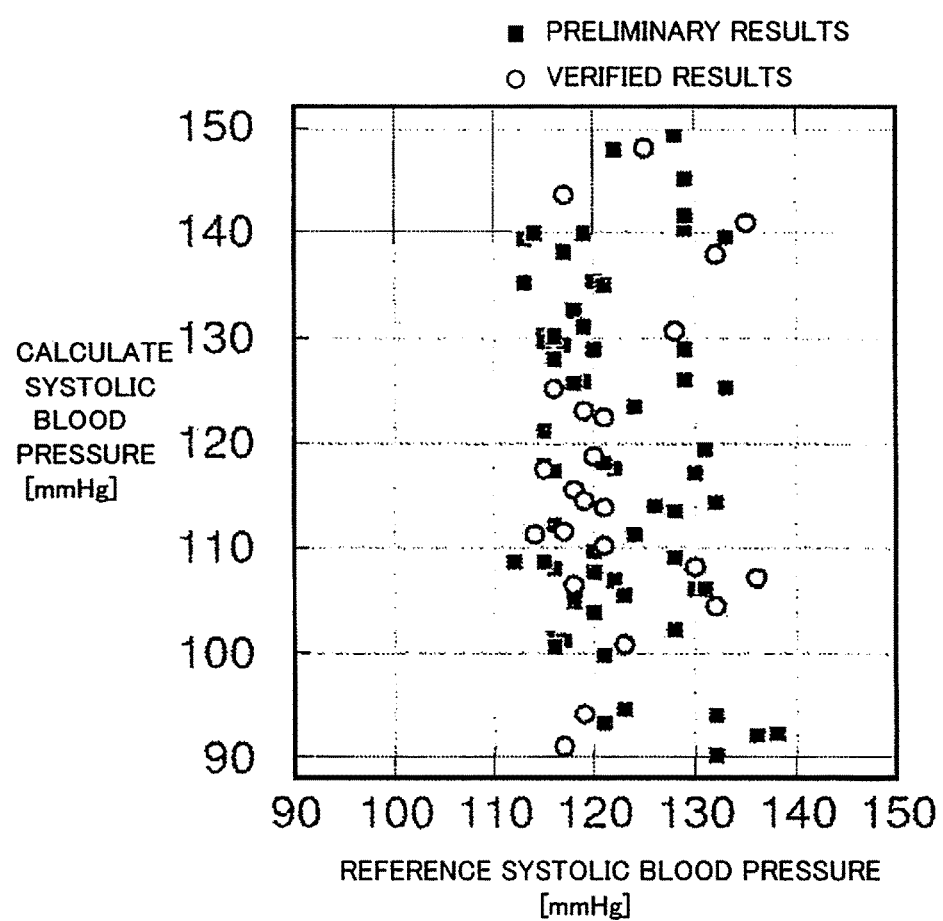
FIG. 7 is a correlation chart showing the correlation between calculated systolic blood pressure, which is estimated from waveform data obtained from performing the time span standardization process on a pulse wave measured at the wrist, and reference systolic blood pressure.

FIG. 6 is a correlation chart showing the correlation between calculated systolic blood pressure, which is an estimated blood pressure value estimated from waveform data after the time span standardization process was performed on a pulse wave measured at the elbow, and reference systolic blood pressure, which is an actual measured blood pressure value. FIG. 7 is a correlation chart showing the correlation between calculated systolic blood pressure, which is an estimated blood pressure value estimated from waveform data after the time span standardization process was performed on a pulse wave measured at the wrist, and reference systolic blood pressure, which is an actual measured blood pressure value.

In these charts, the solid black square marks are estimated blood pressure values obtained through the PLS regression analysis method, by estimating (predicting) blood pressure values from waveform data of measured pulse waves, and the circle marks are verified values. Among the measured data points for the elbow, the number of points that are shown by square marks and used for creating a calibration model is 75, and the number that are shown by circle marks and used for verification is 24.

Table 1 shows the correlation between calibration results for the elbow and wrist shown in FIGS. 6 and 7, and measurement results from the automatic blood pressure gauge. Observing the correlation, the standard estimation error (SEC), and the standard prediction error (SEP) of Table 1, it is clear that with a method of carrying out only the time span standardization process to perform regression analysis, there is a low correlation between estimated values and actual measured values of blood pressure values based on the acquired waveform of the pulse wave.

TABLE 1

| | Factor Number | Correlation Function | SEC [mmHg] | SEP [mmHg] |
|---|---|---|---|---|
| Elbow | 3 | 0.36 | 12 | 17 |
| Wrist | 2 | 0.11 | 23 | 17 |

Figure 8:
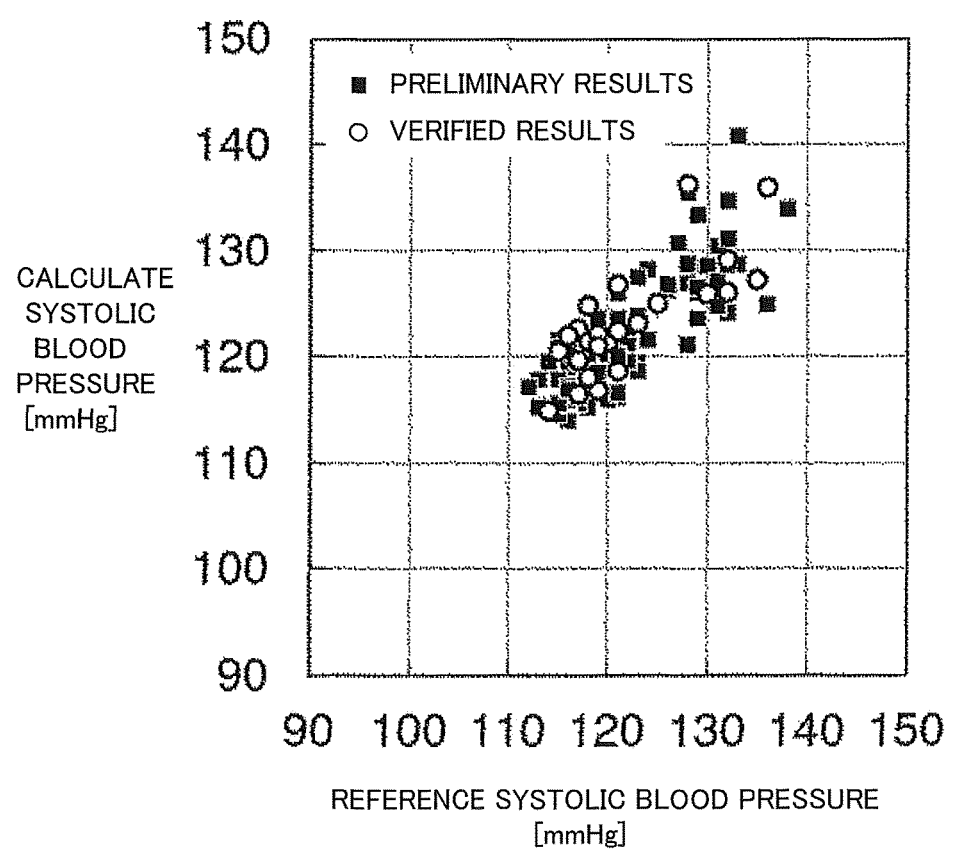
FIG. 8 is a correlation chart showing the correlation between calculated systolic blood pressure estimated from waveform data obtained by performing the time span standardization process and the wavelength displacement standardization process on a pulse wave measured at the elbow, and reference systolic blood pressure.
Figure 9:
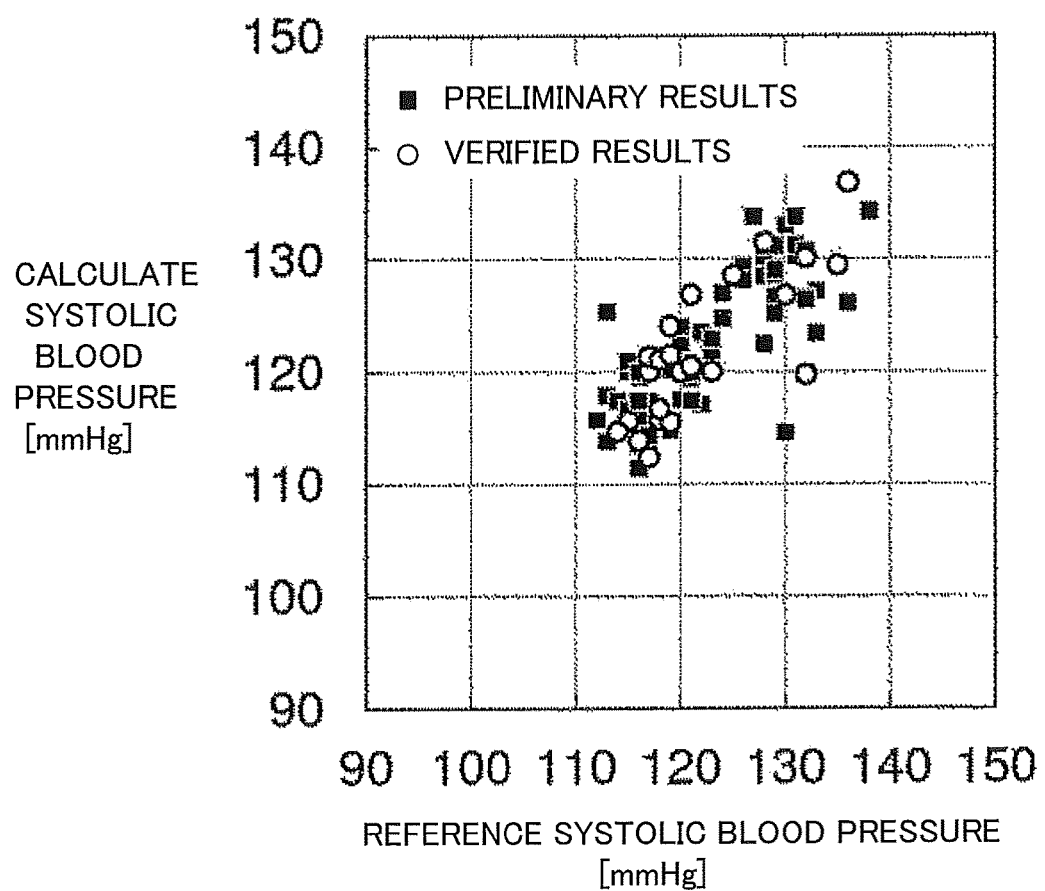
FIG. 9 is a correlation chart showing the correlation between calculated systolic blood pressure estimated from waveform data obtained by performing the time span standardization process and the wavelength displacement standardization process on a pulse wave measured at the wrist, and reference systolic blood pressure.

FIG. 8 is a correlation chart showing the correlation between estimated blood pressure values (calculated systolic blood pressure) estimated by the PLS regression analysis method, and actual measured blood pressure values (reference systolic blood pressure) from the automatic blood pressure gauge, taken from one-cycle waveform data obtained by performing the time span standardization process and the wavelength displacement standardization process on a pulse wave measured at the elbow. FIG. 9 is a correlation chart showing the correlation between estimated blood pressure values (calculated systolic blood pressure) estimated by the PLS regression analysis method, and actual measured blood pressure values (reference systolic blood pressure) from the automatic blood pressure gauge, taken from one-cycle waveform data obtained by performing the time span standardization process and the wavelength displacement standardization process on a pulse wave measured at the wrist. In these charts, the solid black square marks are estimated blood pressure values estimated (predicted) from the pulse wave waveform acquired using the FBG sensor, and the circle marks are verified values.

In the present test, the optimal factor number was 4, and errors were minimal in calibration models having 4 as the factor number. Therefore, correlations were observed for cases in which calibration models having factor numbers of 4 were used.

Table 2 shows the correlations between calibration results and the measurement results from the automatic blood pressure gauge, for the elbow and wrist shown in FIGS. 8 and 9.

TABLE 2

| | Factor Number | Correlation Function | SEC [mmHg] | SEP [mmHg] |
|---|---|---|---|---|
| Elbow | 4 | 0.82 | 4 | 4 |
| Wrist | 4 | 0.78 | 4 | 4 |

As is shown in this table, there is a good correlation between estimated blood pressure values estimated from the waveform data acquired from the FBG sensor, and the actual measured blood pressure values from the automatic blood pressure gauge. The correlation function, the standard estimation error (SEC), and the standard prediction error (SEP) have a higher correlation function than the case of data processing without the wavelength displacement standardization process shown in Table 1. Comparing the waveform data of the elbow and the waveform data of the wrist, the waveform data of the pulse wave acquired from the elbow has the better correlation function.

The wavelength displacement standardization process is believed to have the effect of equalizing nonuniformity in the waveform data caused by factors such as nonuniformity in push pressure when the FBG sensor is attached to the measured location, and positional misalignment of the FBG sensor at the time of measurement. The wavelength displacement standardization process is believed to be effective in minimizing noise caused by such nonuniformity during measurement, and improving the accuracy of the correlation between the waveform data and the actual measured blood pressure values.

Figure 10:
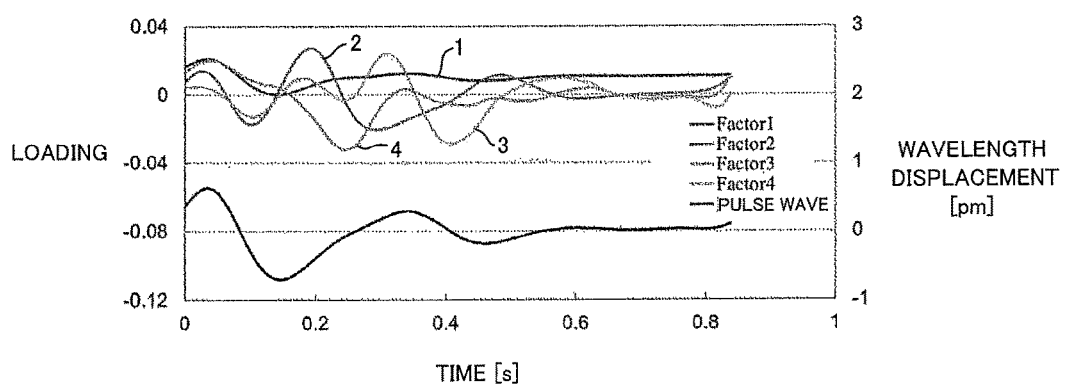
FIG. 10 is a waveform graph showing a loading waveform when a calibration model is constructed from waveform data of a pulse wave measured at the elbow.

FIG. 10 is a waveform graph showing a loading waveform when a calibration model is constructed from waveform data of the acceleration pulse wave measured at the elbow. This loading waveform shows that the one-cycle waveform data of a pulse wave, the data at approximately 0.1 sec and 0.2 sec from the time point when the pulse wave starts has the greatest effect on the calibration model. The systolic blood pressure of the heart is measured in the blood pressure measurement described above. Because the pulse wave reflects data starting from the time the heart begins to contract, data near the beginning of the pulse wave is believed to contribute more to the correlation with the blood pressure values (systolic blood pressure).

(Speculations on Test Results)

The test and analysis results described above show that a subject's blood pressure value can be sufficiently predicted by placing an FBG sensor in a location where the pulse wave is easily measured, such as the subject's elbow or wrist where blood pressure is measured, and acquiring waveform data of the pulse wave.

Specifically, a calibration model (a calibration formula or a calibration curve) representing the correlation between pulse wave waveform data and blood pressure values is constructed on the basis of the correlation between pulse wave waveform data acquired using an FBG sensor and actual measured blood pressure values acquired at the same time that the waveform data is acquired, and after the calibration model has been constructed, pulse wave waveform data is acquired from the subject to estimate (predict) a blood pressure value on the basis of the calibration model.

If a calibration model is constructed, a subject's blood pressure values can be continuously measured by attaching an FBG sensor to a location such as the subject's elbow or wrist where pulse waves are easily detected, and detecting the waveform data of the pulse wave. The FBG sensor is preferably fitted to a single location such as the elbow or wrist. Consequently, sensing of the pulse wave is not affected even if the subject moves their body, and an advantage of this method is that blood pressure can be measured reasonably even when blood pressure is measured continuously.

A calibration model based on the correlation between pulse wave waveform data and actual measured blood pressure values can be shared among different subjects as shown in Test Example 2 described hereinafter, but a calibration model may also be constructed for each subject. For example, in cases such as when the blood pressure measurement device 1 shown in FIG. 1 is used to continuously measure blood pressure, for each subject, pulse wave waveform data and actual measured values of blood pressure are acquired in advance, the operation of constructing a calibration model is performed, and the constructed calibration model is used to measure blood pressure values. Moreover, even with the same subject, it is sometimes acceptable to reconstruct (correct) the calibration model in cases such as when the subject's physical condition or the like has changed over time.

In the present test, analysis was performed with the systolic blood pressure (maximum blood pressure) as the reference blood pressure value. As is shown in Test Example 3 described hereinafter, it is also possible to estimate (predict) diastolic blood pressure on the basis of waveform data detected using an FBG sensor, by finding the correlation with the pulse wave waveform data while using diastolic blood pressure (minimum blood pressure) as the reference blood pressure value.

Test Example 2

Similar to Test Example 1, the pulse wave waveforms of different subjects were measured using an FBG sensor, a calibration model was constructed using the PLS regression analysis method, and the correlation was examined between estimated blood pressure values estimated from the measured waveform data of the pulse waves, and the actual measured blood pressure values measured with an automatic blood pressure gauge.

In the present example, with three men in their twenties as subjects A, B, and C, FBG sensors were secured with medical tape to pulse wave detection locations on their wrists, and pulse waves were measured with the subjects lying supine. The sampling frequency in the pulse wave measurements was 10 kHz. At the same time the pulse wave measurements were taken by the FBG sensors, systolic blood pressures were measured by an automatic blood pressure gauge on the upper arm, and these pressures were used as reference values. For the pulse wave waveform data, data from the start to end of one measurement taken by the automatic blood pressure gauge was acquired as one set, and the pulse wave waveform data was used after being subjected to an equalizing process. Fifty measurements were taken with each subject.

Figure 11:
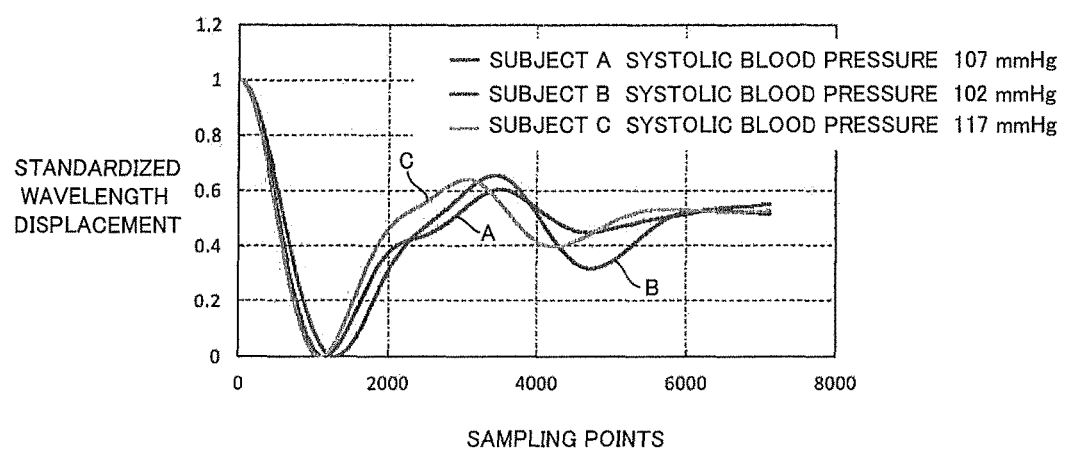
FIG. 11 is a waveform graph showing waveforms after performing the time span standardization process and the wavelength displacement standardization process on one-cycle waveform data of pulse waves measured at the wrists of three subjects.

FIG. 11 is a waveform graph showing waveforms obtained by performing the time span standardization process and the wavelength displacement standardization process on one-cycle waveform data extracted from processing pulse waves measured at the wrists of subjects A, B, and C. Processing the pulse wave waveforms, the purpose of which was to remove noise, involved running the pulse waves through a band-pass filter ($0.5<f<5$), and isolating a pulse wave for each heartbeat with the peak of the pulse wave as a reference point to obtain one-cycle waveform data.

The time span standardization process of isolating each set of one-cycle waveform data was carried out in conformity with the time span of the shortest cycle among the one-cycle waveform data. Furthermore, to reduce noise caused by body movement, multiple sets of one-cycle waveform data (the pulse wave of one heartbeat) appearing within the pulse wave measurement time were equalized, and to eliminate the effects of baseline fluctuation, the wavelength displacement standardization process was performed on each set of one-cycle waveform data with the starting point at 1 and minimum value at 0. It is clear from FIG. 11 that the pulse wave shapes were quite different with each of the subjects A, B, and C.

Next, a calibration model was constructed through the PLS regression analysis method, the explanatory variable being one-cycle waveform data that had been subjected to the time span standardization process and the wavelength displacement standardization process shown in FIG. 11, and the objective variable being reference systolic blood pressure which are actual measured blood pressure values from the automatic blood pressure gauge. 125 data sets from 150 data sets acquired from the subjects A, B, and C were randomly assigned to construct a calibration model, and the remaining 25 data sets were used to verify the calibration model.

Leave-one-out cross-validation was used to evaluate the accuracy of the calibration model. The PLS factor number was increased, and the factor number employed was the factor number at the time F certification had assessed that there was no significant difference in the PRESS value (the sum of squares of the predictive residue).

Here, the accuracy standard for the automatic blood pressure gauge (electronic blood pressure gauge) is stipulated that the average range with auscultation be within 5 mmHg. In the analysis below, the reference value was the systolic blood pressure measured using an automatic blood pressure gauge that met the accuracy standard, and the target was to have the average range with auscultation be within 5 mmHg.

Figure 12:
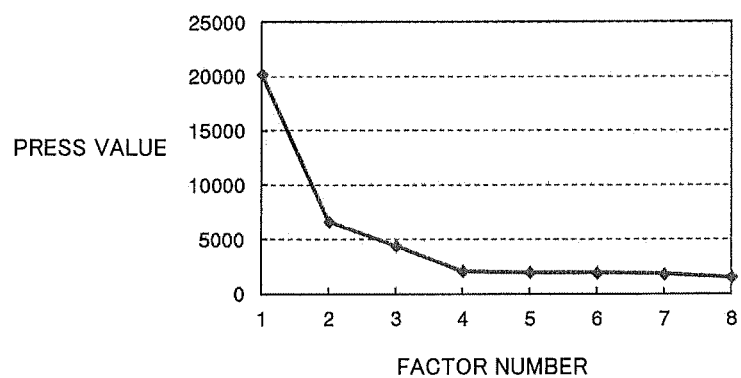
FIG. 12 is a graph showing PRESS values of each PLS factor when cross-validation was performed in the calibration model construction by PLS regression analysis.

FIG. 12 is a graph showing PRESS values of each PLS factor when leave-one-out cross-validation was performed in the calibration model construction by PLS regression analysis. As a result of F certification, it was determined that the difference in PRESS value was not significant between the factor numbers of 8 and 9, and 8 was therefore used as the PLS factor number.

Figure 13:
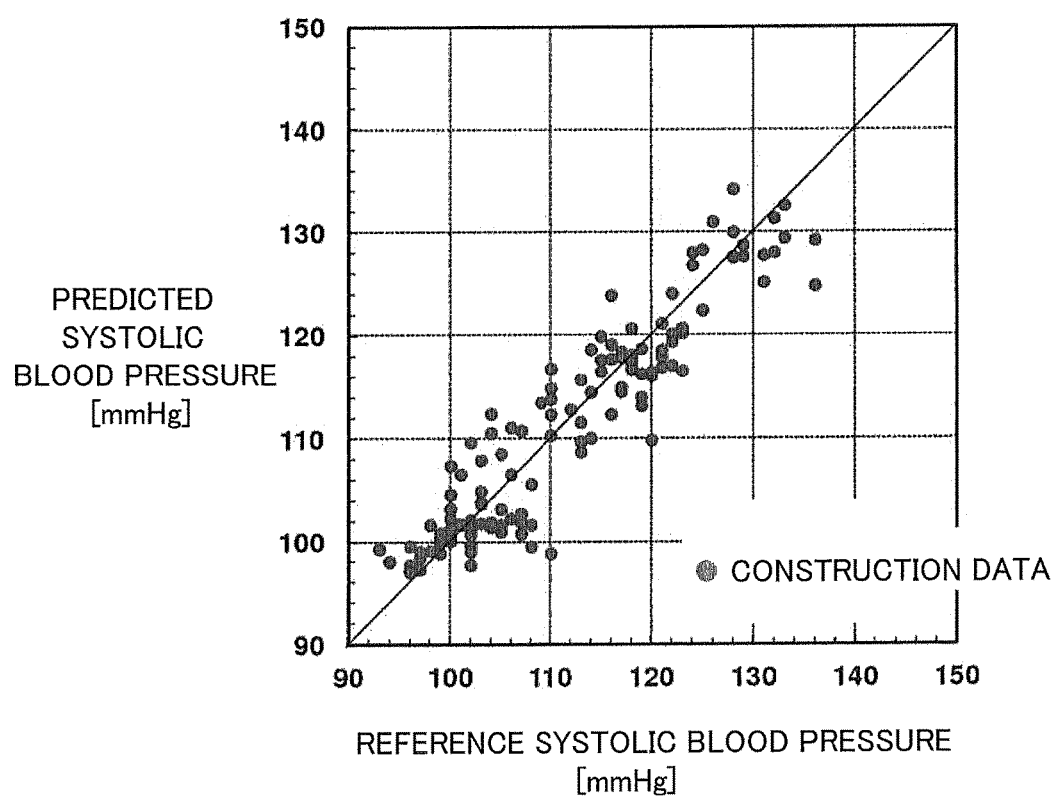
FIG. 13, which is a correlation chart showing the correlation between predicted systolic blood pressure values and reference systolic blood pressure, shows construction data of a calibration model constructed on the basis of waveform data for the wrists of the three subjects shown in FIG. 11.
Figure 14:
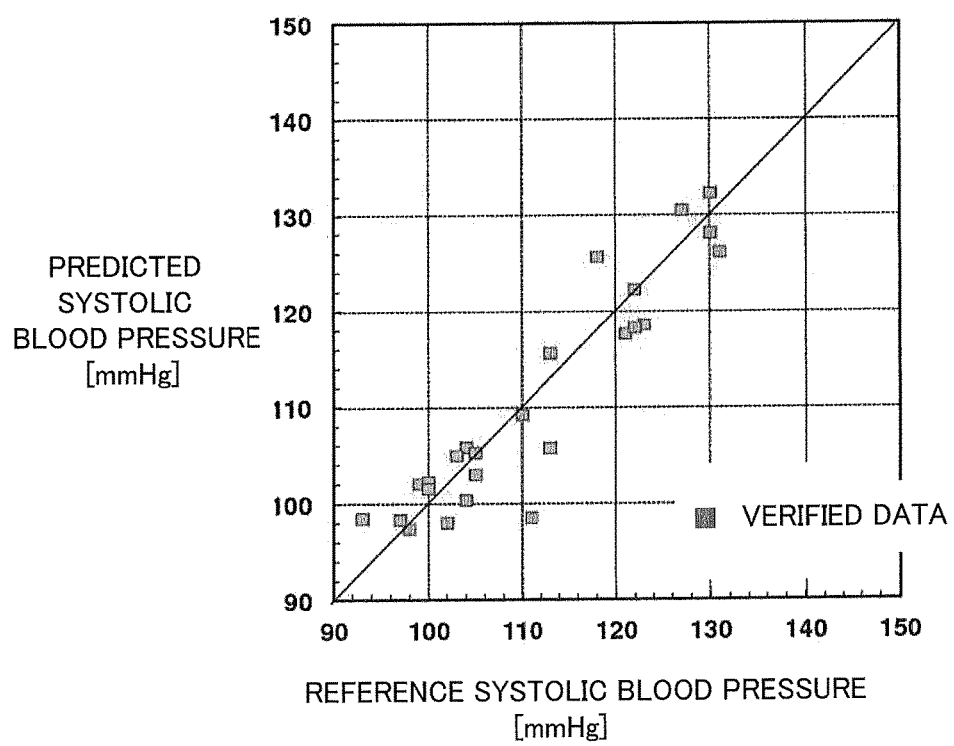
FIG. 14, which is a correlation chart showing the correlation between predicted systolic blood pressure and reference systolic blood pressure, shows the verification results of a calibration model constructed according to the construction data shown in FIG. 13.

FIG. 13, which is a correlation chart showing the correlation between predicted systolic blood pressure values and reference systolic blood pressure values, shows construction data of a calibration model constructed on the basis of waveform data for the wrists of the three subjects A, B, and C shown in FIG. 11. FIG. 14 is a correlation chart showing the correlation between predicted systolic blood pressure and reference systolic blood pressure, in which the verification results of the calibration model are plotted.

Table 3 is a compilation of the construction results of the calibration model, and Table 4 is a compilation of the verification results. It is clear from Table 3 that the correlation between the predicted values of the calibration model and the blood pressure reference values has a high degree of significance, and the target accuracy was achieved for the average range. Table 4 yielded the results that the average range of the verification results was 3 mmHg, and systolic blood pressure can be estimated (can be predicted) with high accuracy.

TABLE 3

| Construction Points | Average Value (mmHg) | Minimum Value (mmHg) | Maximum value (mmHg) |
|---|---|---|---|
| 125 | 112 | 93 | 136 |
| PLS analysis results | | Factor number 8 | |
| | | Correlation 0.93 | |
| | | Average range (mmHg) 3 | |

TABLE 4

| Construction Points | Average Value (mmHg) | Minimum Value (mmHg) | Maximum value (mmHg) |
|---|---|---|---|
| 25 | 11 | 93 | 131 |
| PLS analysis results | | Average range (mmHg) 3 | |

Next, an FBG sensor was used to measure pulse waves with three subjects D, E, and F other than the subjects A, B, and C used to construct the calibration model. Twenty-five measurements were taken with each subject. Using the waveform data of the measured pulse waves, verification was performed on the calibration model constructed as described above.

Figure 15:
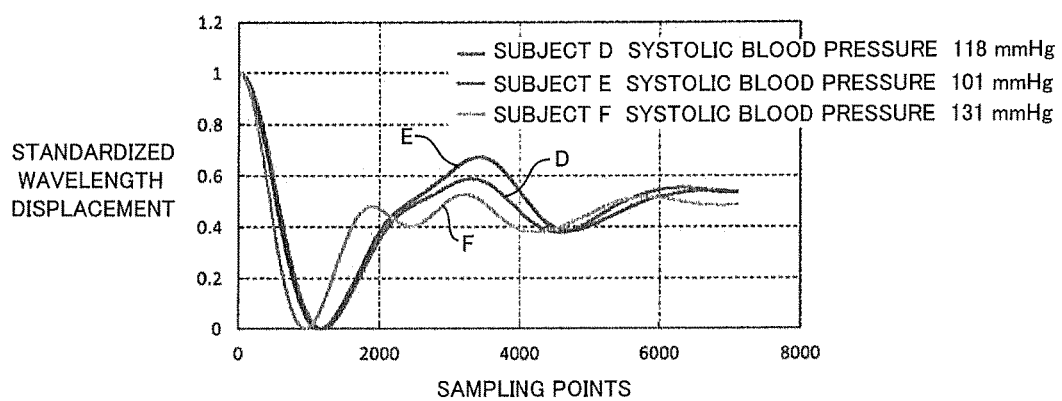
FIG. 15 is a waveform graph showing waveforms after the time span standardization process and the wavelength displacement standardization process has been performed on one-cycle waveform data of pulse waves measured on the wrists of three subjects.
Figure 16:
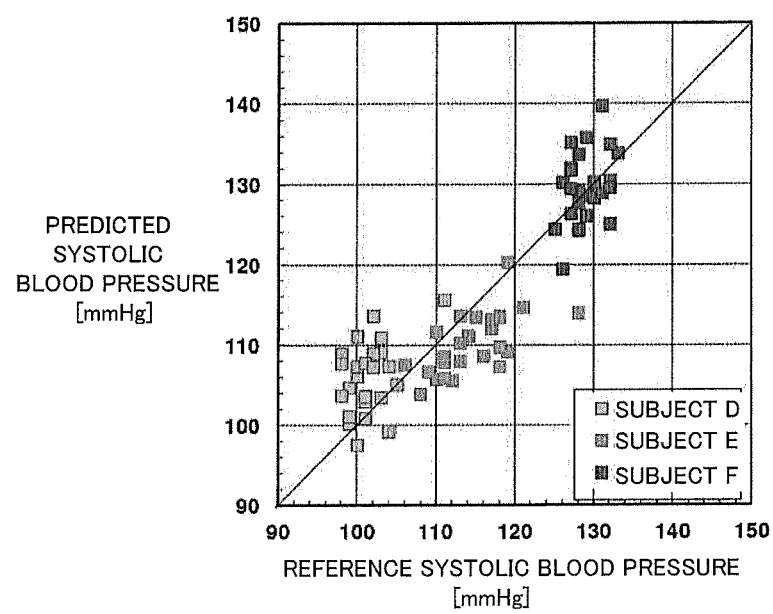
FIG. 16, which is a correlation chart showing the correlation between predicted systolic blood pressure and reference systolic blood pressure, shows the verification results of the calibration model constructed according to the construction data shown in FIG. 13.

FIG. 15 is a waveform graph showing waveforms obtained by performing the time span standardization process and the wavelength displacement standardization process on one-cycle waveform data of pulse waves measured on the wrists of the three subjects D, E, and F. The correlation chart shown in FIG. 16, showing the difference between predicted systolic blood pressure and reference systolic blood pressure, shows the verification results of the calibration model.

Table 5 shows the average range of the subjects D, E, and F and the average range of all of the subjects. In Table 5, although the average range of all of the subjects meets the target accuracy, the target accuracy is not met with subject E.

TABLE 5

| | Subject D | Subject E | Subject F | All subjects |
|---|---|---|---|---|
| Average range (mmHg) | 4.8 | 5.1 | 3.4 | 4.4 |

In Table 5, the reason that subject E alone did not meet the target accuracy was presumably because there were numerous instances of a PLS factor number of 8 and there was a possibility of overfitting. In view of this, the factor number was changed from 1 to 8, a new calibration model was constructed, and the pulse waves of subjects D, E, and F were used to conduct verification. The factor number verification results are shown in Table 6.

TABLE 6

| | Average Range [mmHg] | | | |
|---|---|---|---|---|
| Factor number | Subject D | Subject E | Subject F | All subjects |
| Factor 1 | 5.6 | 12.0 | 18.0 | 12.2 |
| Factor 2 | 4.3 | 8.9 | 3.1 | 5.5 |
| Factor 3 | 4.0 | 6.9 | 2.7 | 4.5 |
| Factor 4 | 3.5 | 3.8 | 2.3 | 3.2 |
| Factor 5 | 3.1 | 4.7 | 3.7 | 3.8 |
| Factor 6 | 3.3 | 5.0 | 3.1 | 3.8 |
| Factor 7 | 3.3 | 6.6 | 2.7 | 4.2 |
| Factor 8 | 4.8 | 5.1 | 3.4 | 4.4 |

The values inside the rectangular frames in Table 6 are the minimum values in each column. When the factor number is 4, the average ranges reach a minimum value for subjects E and F and for all subjects, and when the factor number is 5, the average range reaches a minimum value for subject D. The average range of subject D is 3.5 mmHg at the factor number of 4, which is a sufficiently small range, and it is therefore possible for 4 to be the optimum factor number.

Figure 17:
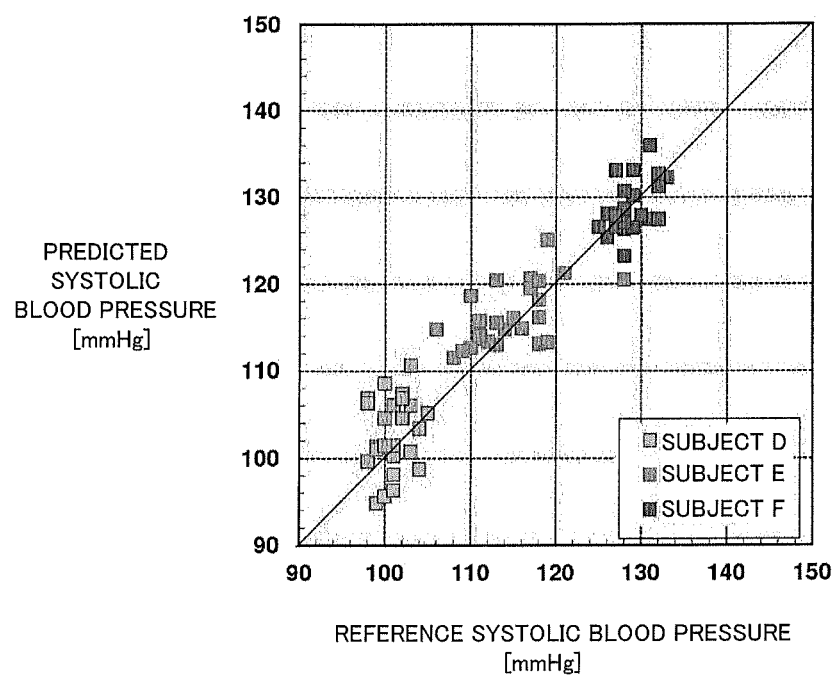
FIG. 17, which is a correlation chart showing the correlation between predicted systolic blood pressure and reference systolic blood pressure, shows the verification results of a calibration model obtained by reconstructing the calibration model shown in FIG. 13 using 4 as the factor number.

The correlation chart shown in FIG. 17, which shows the correlation between predicted systolic blood pressure and reference systolic blood pressure, shows the verification results when the calibration model is reconstructed using 4 as the factor number. At 0.95, the correlation between reference values and predicted values is highly significant, and the target accuracy is met for all subjects as well.

As described above, the reconstructed calibration model demonstrates that blood pressure values can be estimated with sufficient accuracy, even when a calibration model (a calibration formula or a calibration curve) constructed on the basis of acquired data on the subjects A, B, and C is applied to other subjects D, E, and F. Consequently, this demonstrates the possibility that the blood pressure estimation method of the present invention could be utilized as a versatile blood pressure measurement method. Specifically, this suggests the possibility that one calibration model could be utilized in a versatile manner with no need for an operation such as correcting the calibration model for each subject in advance.

Test Example 3

Test Examples 1 and 2 above are both examples in which systolic blood pressure was estimated (predicted) from pulse waves acquired using an FBG sensor. In the present test example, diastolic blood pressure was estimated from waveform data of acquired pulse waves.

Similar to the cases of Test Examples 1 and 2, pulse waves were measured both from an FBG sensor attached to the wrist and an FBG sensor attached to the elbow, and at the same time, an automatic blood pressure gauge was used to monitor diastolic blood pressure as the blood pressure values of the subjects. Pulse waves were measured 100 times, and the sampling frequency was 10 kHz.

Figure 18:
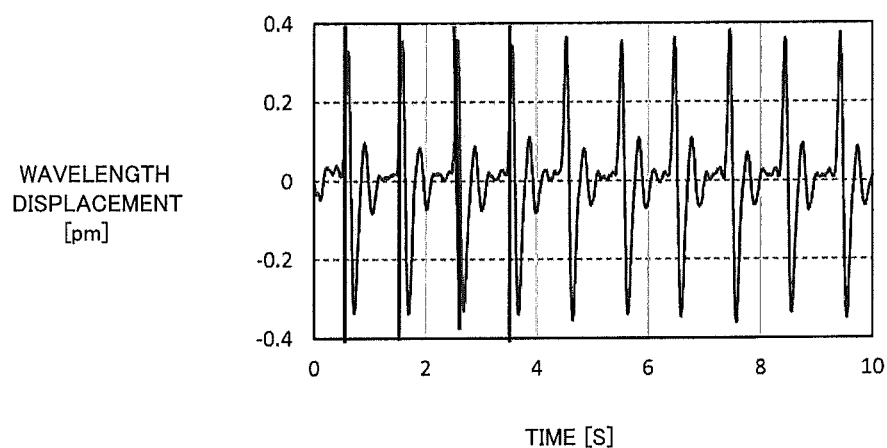
FIG. 18 is a waveform graph showing the waveform obtained after a pulse wave measured using an FBG sensor is run through a filter in order to remove noise.

FIG. 18 is a waveform graph showing the waveform obtained after a pulse wave measured using an FBG sensor is run through a filter in order to remove noise. With the peak position as a reference, one-cycle waveform data is extracted in each pulse from one set of pulse wave data acquired in one blood pressure estimation, these data sets are averaged to calculate average waveform data, and the calculated one-cycle average waveform data is used as basic data for analysis.

FIGS. 19 to 22, which are waveform graphs showing one-cycle waveform data of pulse waves obtained when the diastolic blood pressure is 63 mmHg, 65 mmHg, and 75 mmHg, each show a case in which a standardization process is carried out in a different form.

Figure 19:
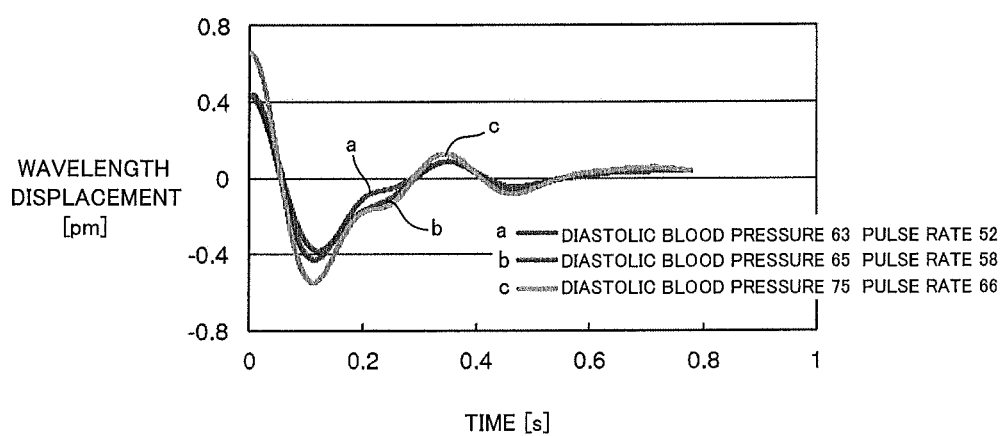
FIG. 19 is a waveform graph showing one-cycle waveform data of pulse waves obtained when diastolic blood pressure differs.
Figure 20:
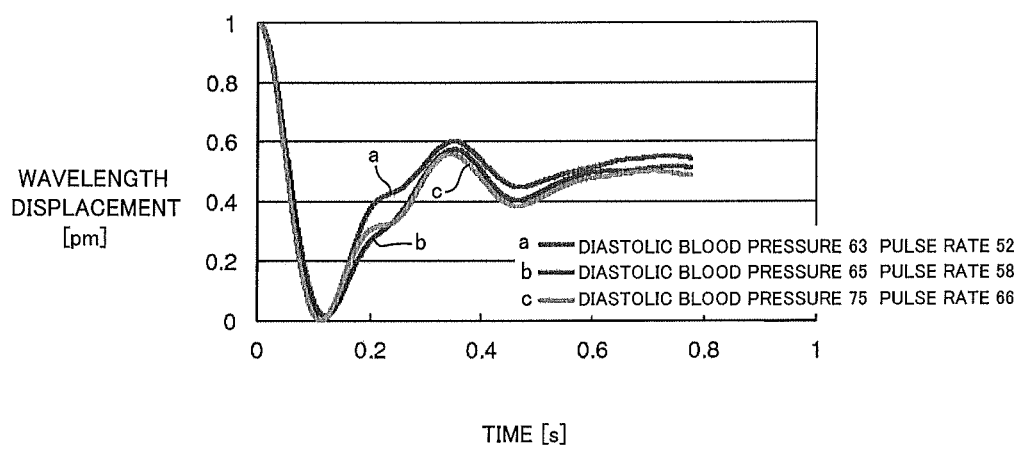
FIG. 20 is a waveform graph showing waveforms after the wavelength displacement standardization process has been carried out on the one-cycle waveform data of FIG. 19 so that the height is 1.
Figure 21:
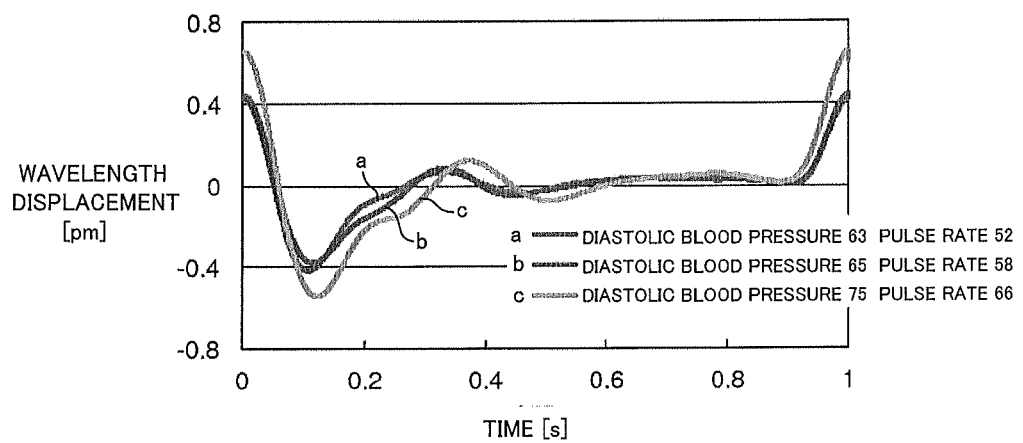
FIG. 21 is a waveform graph showing waveforms after the time span standardization process has been carried out on the one-cycle waveform data of FIG. 19 so that the length is 1.
Figure 22:
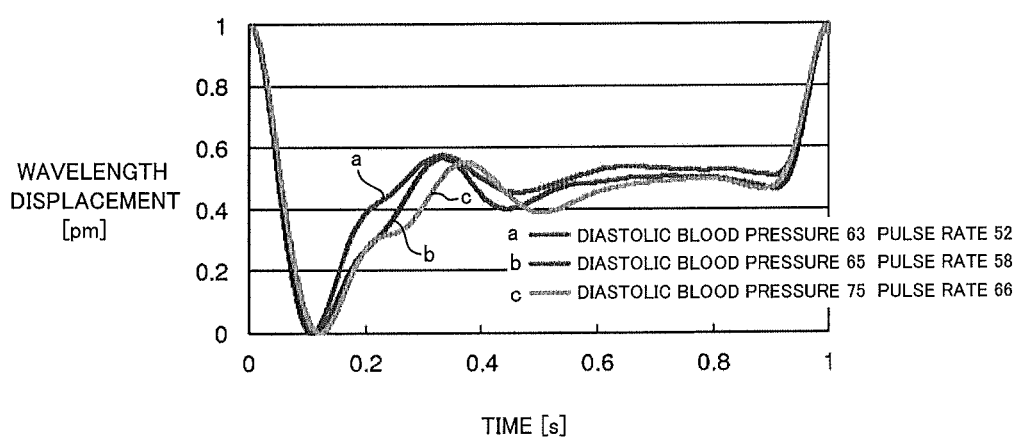
FIG. 22 is a waveform graph showing waveforms after the wavelength displacement standardization process and the time span standardization process have been carried out on the one-cycle waveform data of FIG. 19 so that the height and length are 1.
Figure 23:
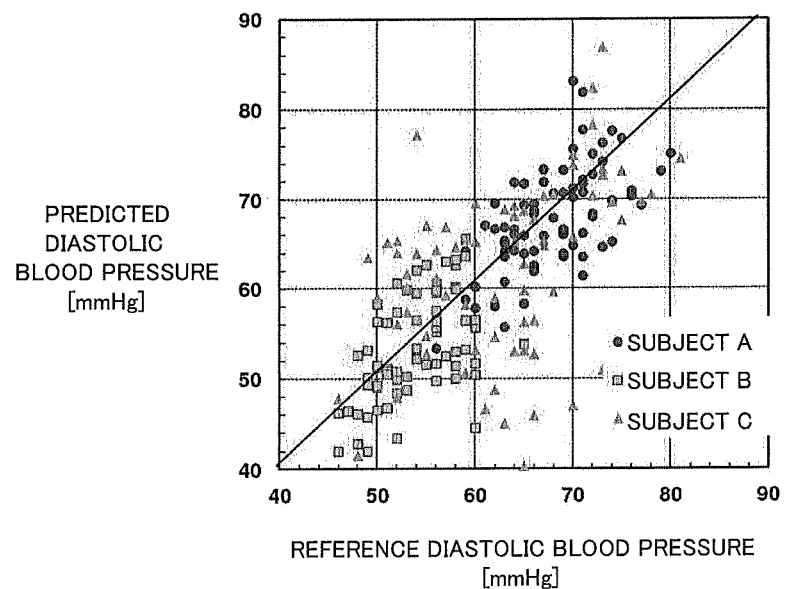
FIG. 23 is a correlation chart showing the correlation between reference diastolic blood pressure and predicted diastolic blood pressure estimated from one-cycle waveform data of pulse waves measured at the wrists of three subjects.
Figure 24:
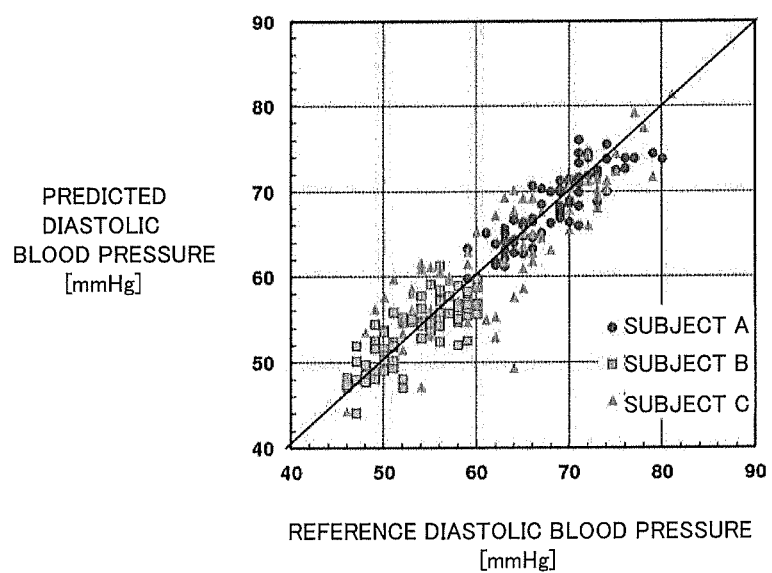
FIG. 24 is a correlation chart showing the correlation between reference diastolic blood pressure and predicted diastolic blood pressure estimated from waveform data after the wavelength displacement standardization process had been performed on one-cycle waveform data of pulse waves measured at the wrists of three subjects.
Figure 25:
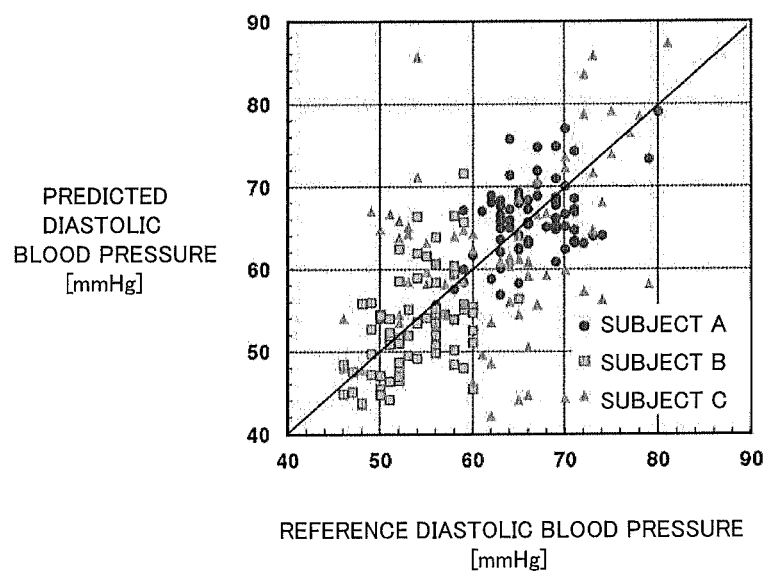
FIG. 25 is a correlation chart showing the correlation between reference diastolic blood pressure and predicted diastolic blood pressure estimated from waveform data after the time span standardization process had been performed on one-cycle waveform data of pulse waves measured at the wrists of three subjects.

In FIG. 19, a time span standardization process is carried out in which the data sets are sectioned by the minimum time span of the pulse wave. FIG. 20 is a waveform graph showing waveforms obtained by carrying out the wavelength displacement standardization process on the one-cycle waveform data of FIG. 19, so that the height is 1. FIG. 21 is a waveform graph showing waveforms in a case in which the time span standardization process has been carried out on the one-cycle waveform data so that the length (time) is 1. FIG. 22 is a waveform graph showing waveforms in a case in which the wavelength displacement standardization process has been carried out on the waveforms shown in FIG. 21 so that the height is also 1.

The method of standardizing the time span could be a method of extracting pulse wave waveform data in a minimum time span such as is shown in FIG. 19, or a method of standardizing the time span to 1 (sec) such as is shown in FIG. 21, but there was confirmed to be no difference in estimation accuracy with either method.

Figure 26:
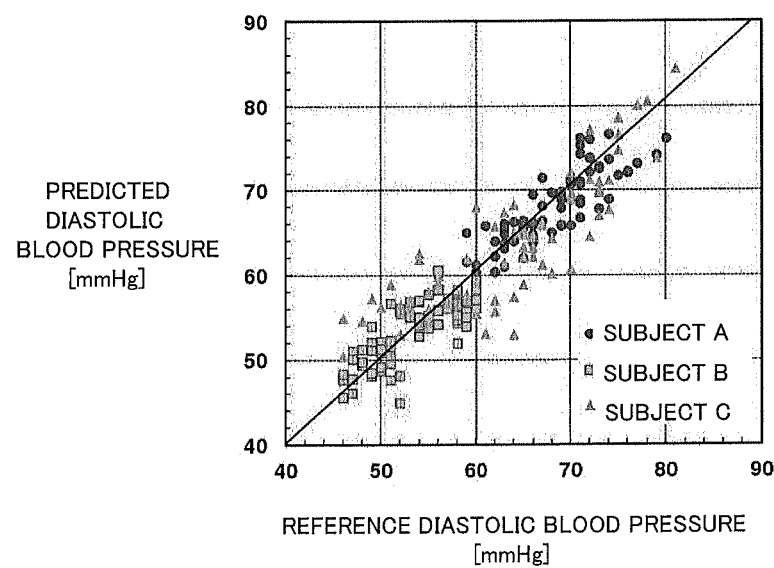
FIG. 26 is a correlation chart showing the correlation between reference diastolic blood pressure and predicted diastolic blood pressure estimated from waveform data after both the wavelength displacement standardization process and the time span standardization process had been performed on one-cycle waveform data of pulse waves measured at the wrists of three subjects.
Figure 27:
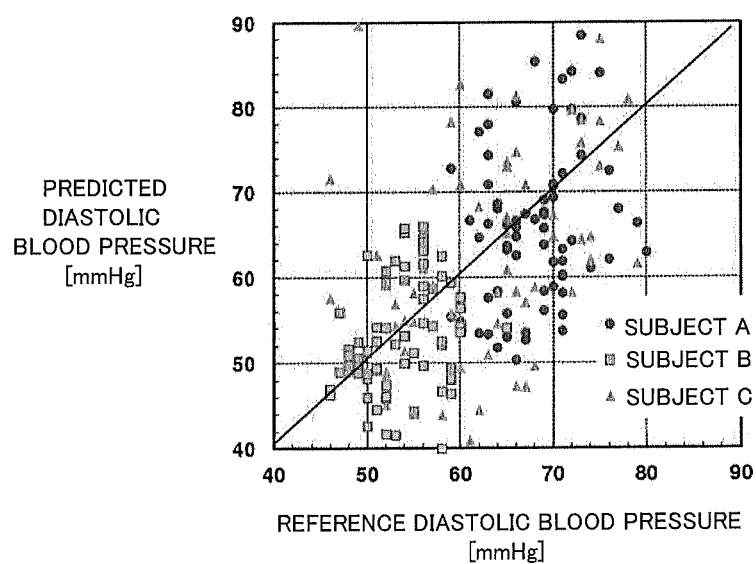
FIG. 27 is a correlation chart showing the correlation between reference diastolic blood pressure and predicted diastolic blood pressure estimated from one-cycle waveform data of pulse waves measured at the elbows of three subjects.
Figure 28:
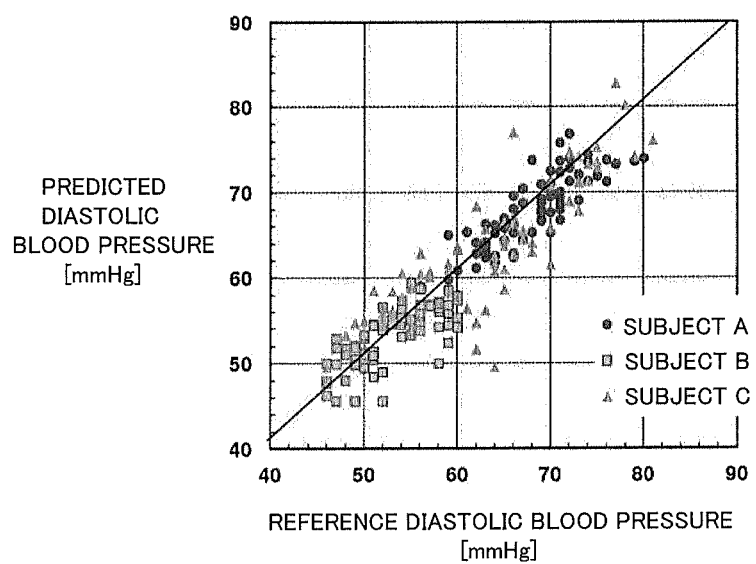
FIG. 28 is a correlation chart showing the correlation between reference diastolic blood pressure and predicted diastolic blood pressure in a case of using waveform data after the wavelength displacement standardization process had been performed on the one-cycle waveform data, shown in FIG. 27, of pulse waves measured at the elbows of three subjects.
Figure 29:
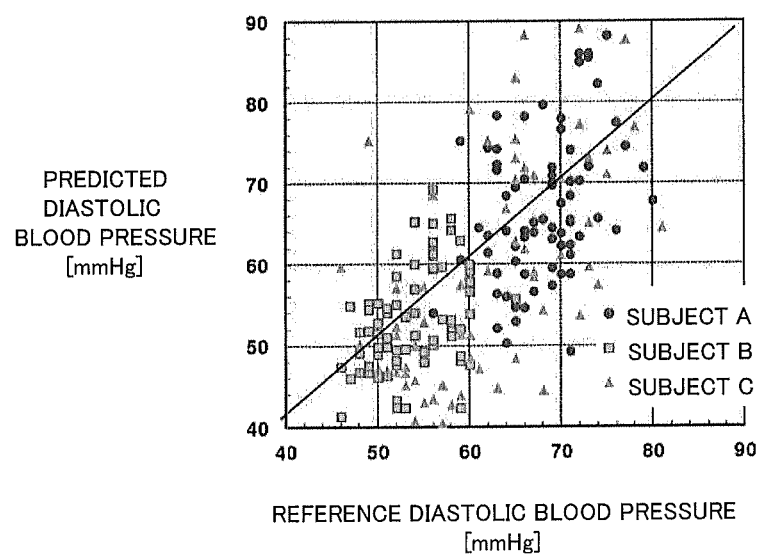
FIG. 29 is a correlation chart showing the correlation between reference diastolic blood pressure and predicted diastolic blood pressure in a case of using waveform data after the time span standardization process had been performed on the one-cycle waveform data, shown in FIG. 27, of pulse waves measured at the elbows of three subjects.

The correlation charts shown in FIGS. 23 to 26, which show the correlation between predicted diastolic blood pressure and reference diastolic blood pressure, show the correlation between estimated values (predicted diastolic blood pressure) from the calibration model constructed through the PLS regression analysis method and actual measured values (reference diastolic blood pressure), in the following cases of processing waveform data of pulse waves acquired from the wrists of the subjects A, B, and C, respectively: a standardization process is not performed (FIG. 23), only the wavelength displacement standardization process is performed (FIG. 24), only the time span standardization process is performed (FIG. 25), and both the wavelength displacement standardization process and the time span standardization process are performed (FIG. 26).

Figure 30:
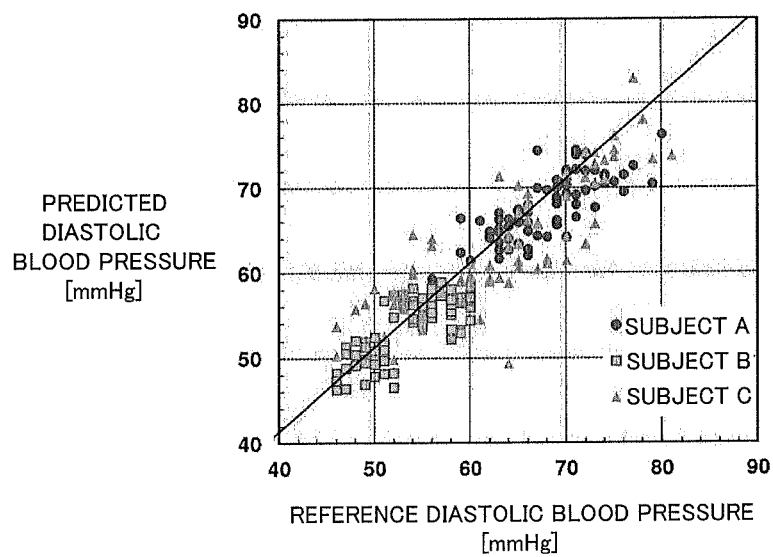
FIG. 30 is a correlation chart showing the correlation between reference diastolic blood pressure and predicted diastolic blood pressure estimated from waveform data after both the wavelength displacement standardization process and the time span standardization process had been performed on the one-cycle waveform data, shown in FIG. 27, of pulse waves measured at the elbows of three subjects.

The correlation charts shown in FIGS. 27 to 30, which show the correlation between predicted diastolic blood pressure and reference diastolic blood pressure, show the correlation between estimated values (predicted diastolic blood pressure) from the calibration model constructed through the PLS regression analysis method and actual measured values (reference diastolic blood pressure), in the following cases of processing waveform data of pulse waves acquired from the elbows of the subjects A, B, and C, respectively: a standardization process is not performed (FIG. 27), only the wavelength displacement standardization process is performed (FIG. 28), only the time span standardization process is performed (FIG. 29), and both the wavelength displacement standardization process and the time span standardization process are performed (FIG. 30).

To examine the correlation between diastolic blood pressure and estimated values of blood pressure according to the calibration model constructed through the PLS regression analysis method, 75 data sets were taken randomly from among the 100 data sets for the subjects A, B, and C, and a calibration model was constructed. The remaining 25 data sets were used to conduct verification on the calibration model. Tables 7, 8, and 9 show the verification results for the subjects A, B, and C.

TABLE 7

| Standardizing Method | Measurement Location | Factor No. | Correlation | Construction Results Av. Range (mmHg) | Verified Results Av. Range (mmHg) |
| --- | --- | --- | --- | --- | --- |
| No standardization | wrist | 4 | 0.59 | 4 | 5 |
| | elbow | 4 | 0.32 | 8 | 10 |
| Wave displacement standardization | wrist | 4 | 0.88 | 2 | 2 |
| | elbow | 4 | 0.85 | 2 | 2 |
| Time span standardization | wrist | 4 | 0.46 | 4 | 6 |
| | elbow | 4 | 0.44 | 8 | 11 |
| Wave dis./time span standardization | wrist | 4 | 0.85 | 2 | 2 |
| | elbow | 4 | 0.77 | 2 | 2 |

TABLE 8

| Standardizing Method | Measurement Location | Factor No. | Correlation | Construction Results Av. Range (mmHg) | Verified Results Av. Range (mmHg) |
| --- | --- | --- | --- | --- | --- |
| No standardization | wrist | 4 | 0.49 | 4 | 4 |
| | elbow | 4 | 0.29 | 5 | 7 |
| Wave displacement standardization | wrist | 4 | 0.79 | 2 | 3 |
| | elbow | 4 | 0.75 | 2 | 3 |
| Time span standardization | wrist | 4 | 0.43 | 5 | 5 |
| | elbow | 4 | 0.37 | 5 | 6 |
| Wave dis./time span standardization | wrist | 4 | 0.79 | 2 | 3 |
| | elbow | 4 | 0.78 | 2 | 3 |

TABLE 9

| Standardizing Method | Measurement Location | Factor No. | Correlation | Construction Results Av. Range (mmHg) | Verified Results Av. Range (mmHg) |
| --- | --- | --- | --- | --- | --- |
| No standardization | wrist | 4 | 0.45 | 9 | 14 |
| | elbow | 4 | 0.32 | 12 | 19 |
| Wave displacement standardization | wrist | 4 | 0.85 | 4 | 4 |
| | elbow | 4 | 0.86 | 4 | 4 |
| Time span standardization | wrist | 4 | 0.37 | 9 | 15 |
| | elbow | 4 | 0.35 | 14 | 16 |
| Wave dis./time span standardization | wrist | 4 | 0.85 | 4 | 5 |
| | elbow | 4 | 0.83 | 4 | 4 |

Tables 7, 8, and 9 show that wavelength displacement standardization is more effective than time span standardization in improving prediction accuracy. These tables also show that the international standard of having an average range within 5 mmHg is met, i.e., diastolic blood pressure can be estimated (predicted) with sufficient accuracy on the basis of the waveform data of pulse waves, by performing wavelength displacement standardization or performing both wavelength displacement standardization and time span standardization.

Figure 31A:
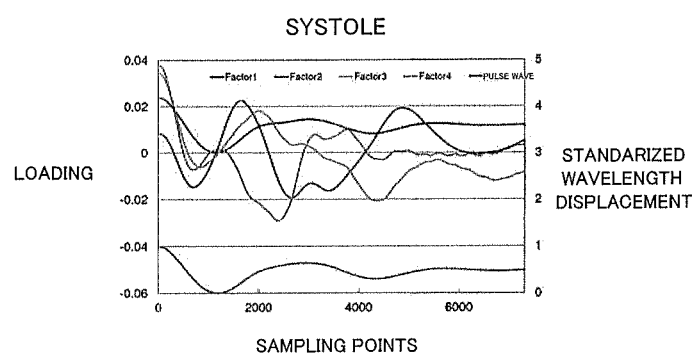
FIG. 31 includes waveform graphs showing loading waveforms when a calibration model is constructed from waveform data of pulse waves.
Figure 31B:
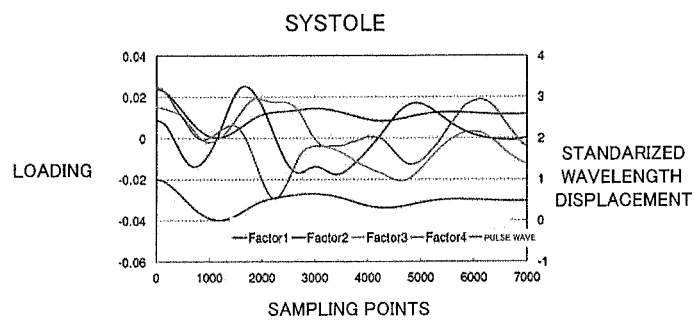

FIG. 31 includes waveform graphs showing loading waveforms when a calibration model is constructed from waveform data of pulse waves. FIG. 31(a) shows loading waveforms when a calibration model of systole is constructed, and FIG. 31(b) shows loading waveforms when a calibration model of diastole is constructed. Both show loading waveforms up to the factor 4.

Figure 32A:
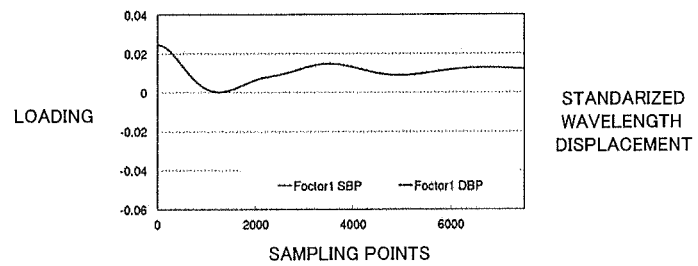
FIG. 32 includes waveform graphs showing only the waveforms of factors 1, 2, and 3 in the loading waveforms of FIG. 31.
Figure 32B:
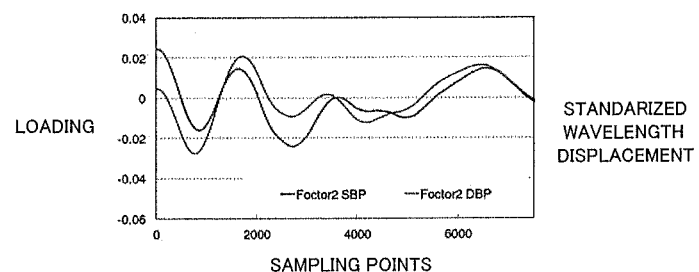
Figure 32C:
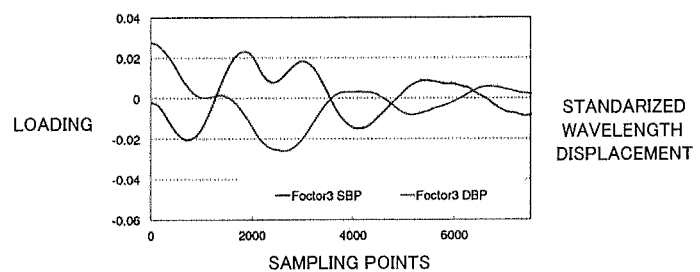

FIG. 32 includes waveform graphs showing only the waveforms of factors 1, 2, and 3, respectively, for systole (SBP) and diastole (DBP) in the loading waveforms of FIG. 31. FIG. 32(a) is a loading waveform of factor 1, FIG. 32(b) is a loading waveform of factor 2, and FIG. 32(c) is a loading waveform of factor 3.

The waveforms of the factors are not always constant; therefore, though it is not necessarily always the case, systole and diastole mostly coincide for factor 1, and for factors 2 and 3, a difference in waveforms between systole and diastole is usually observed. Specifically, factors 2 and 3 are believed to contribute to the differences between the calibration models for systole and diastole.

Figure 33:
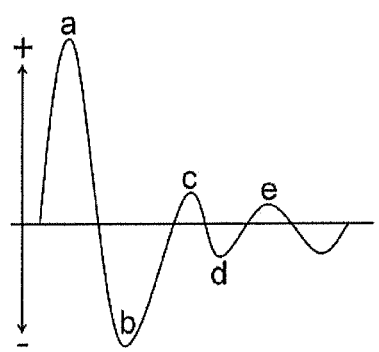
FIG. 33 is a waveform graph showing the basic waveform of one pulse of a pulse wave measured by an FBG sensor.

FIG. 33 is a waveform graph showing the basic waveform for one pulse of a pulse wave measured by an FBG sensor. This basic waveform is equivalent to one pulse of the waveform shown in FIG. 18. In this graph, the a wave is a protosystolic positive wave, the b wave is a protosystolic negative wave, the c wave is a midsystolic re-elevation wave, the d wave is a late systolic re-descent wave, and the e wave is a protodiastolic positive wave. The a wave and the b wave, forward components of systole, are equivalent to driving pressure waves when the heart contracts and pushes out blood, and the c wave and the e wave are equivalent to reflected pressure waves resulting from the driving pressure propagating to dissolution and being reflected back.

Figure 34:
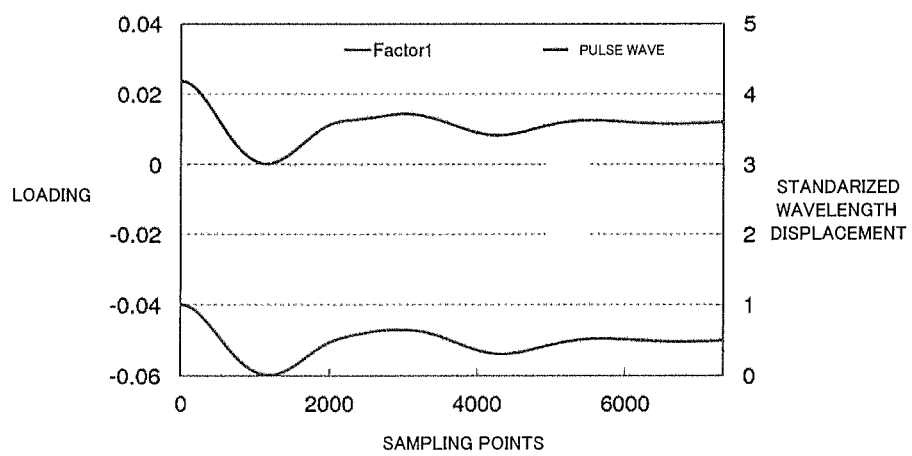
FIG. 34 includes waveform graphs showing the waveform for one pulse of a pulse wave measured by an FBG sensor and the waveform of factor 1 shown in FIG. 32.

FIG. 34 is a waveform graph is a waveform graph showing the waveform for one pulse of a pulse wave measured by an FBG sensor and the waveform of factor 1 shown in FIG. 32. Observing these two waveforms shows that the profiles coincide well with each other. Because of this, factor 1 is believed to have information for both the driving pressure wave and the reflected pressure wave of the pulse wave, and the central blood pressure is predicted. Factors 2, 3, and 4, of which the waveforms differ between systole and diastole, are believed to relate to predicting systolic blood pressure and diastolic blood pressure. The e wave of the pulse wave originates from the diastole of the heart, and is therefore believed to pertain to diastolic blood pressure.

Figure 35A:
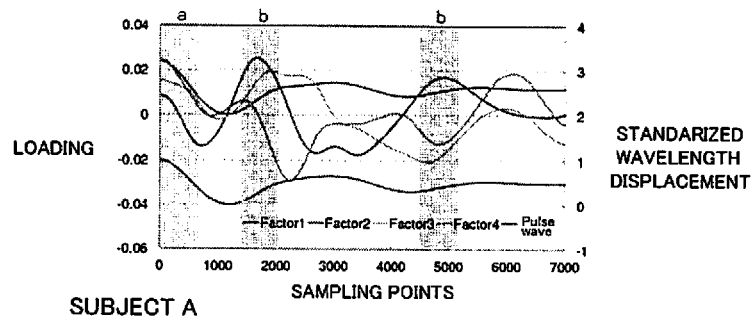
FIG. 35 includes waveform graphs showing loading waveforms when calibration models are constructed from waveform data of pulse waves for three subjects.

FIGS. 35(a), (b), and (c) are waveform graphs showing loading waveforms when calibration models are constructed from waveform data of pulse waves for the subjects A, B, and C. In these drawings, the areas indicated by the letter a are areas having a positive correlation with many factors, and are believed to include much information on the protosystolic blood pressure of the heart. The areas indicated by the letter b are areas where factor 2 has a positive correlation, indicating that at mid-systole of the heart, the reflected wave component contributes to blood pressure prediction.

Figure 35B:
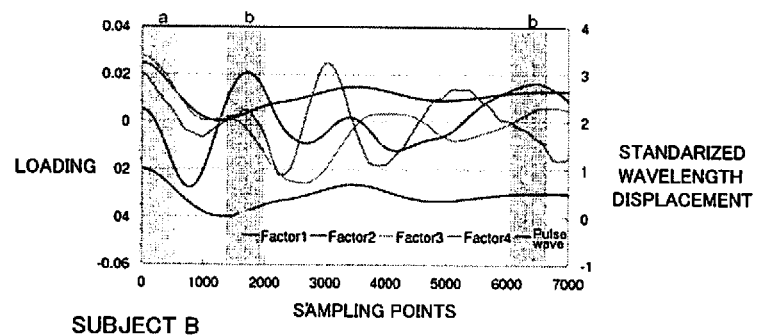
Figure 35C:
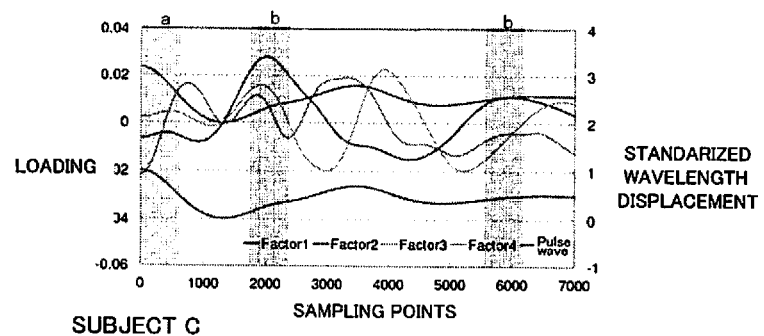

In the loading waveforms in FIG. 35, the positional relationship in the arrangement of the areas indicated by the letter a and the areas indicated by the letter b is the same among the subjects A, B, and C. This common point among the loading waveforms means that there is commonality in the potential factors of pulse waves pertaining to blood pressure, indicating that the results of calibration models through regression analysis are not greatly affected by individual people, i.e., it is possible that the method of the present invention could be utilized in a versatile matter as a blood pressure estimation method.

As described above, the results of the present test indicate that the waveform data of a pulse wave has a correlation with diastolic blood pressure, and also indicates that systolic blood pressure and diastolic blood pressure can both be estimated by acquiring pulse wave data. Specifically, the results indicate that by performing regression analysis on the basis of waveform data of an acquired pulse wave, a calibration model for estimating blood pressure values can be constructed, and it is possible to predict both systolic blood pressure and diastolic blood pressure on the basis of the calibration model.

Other Embodiments

In the above embodiment, an FBG sensor was used as the method of acquiring waveform data of pulse waves. An FBG sensor has extremely high capability to sense distortion (deformation), and has the feature of being able to sense minute distortions such as pulse waves with great accuracy. In the test examples described above, the sampling frequency was 10 kHz, and using a regression analysis method, the international standard accuracy of 5 mmHg was achieved for the average range. The reason such highly accurate estimation is possible is because an FBG sensor has a sensing capability that enables highly accurate analysis.

Therefore, if the sensor has sensing capability similar to an FBG sensor, a sensor other than an FBG sensor can be used in the same manner. For example, sheet-shaped capacitive pressure-sensitive sensors and tactile array sensors are capable of sensing pressure with high accuracy. Consequently, these sensors could be used in place of the FBG sensor.

In the above embodiment, the PLS regression analysis method was employed as the regression analysis method. Another regression analysis method can be used to construct a calibration model, and blood pressure values can be estimated with predetermined accuracy from the waveform data of a pulse wave.

The invention claimed is:

1. A blood pressure estimation method comprising:
measuring an acceleration pulse wave using a fiber Bragg grating sensor;
constructing a calibration model that represents a correlation between measured waveform data of the measured acceleration pulse wave and measured blood pressure values measured at individual measurement time points of the measured waveform data; and
with a processor, using the calibration model to estimate blood pressure values of a subject at a time of an acceleration pulse wave measurement, from the waveform data of the acceleration pulse wave measured from the subject,
wherein the calibration model is constructed by:
extracting a plurality of sets of one-cycle waveform data from the measured waveform data;
standardizing each set of extracted one-cycle waveform data either so that an amount of wavelength displacement is the same or so that the amount of wavelength displacement and a time span are the same; and performing regression analysis with standardized one-cycle waveform data as an explanatory variable and the measured blood pressure value as an objective variable.

2. The blood pressure estimation method according to claim 1,
wherein the calibration model is either one of a first calibration model and a second calibration model,
the first calibration model representing a correlation between the measured waveform data and systolic blood pressure values as the measured blood pressure values, and a second calibration model representing a correlation between the measured waveform data and diastolic blood pressure values as the measured blood pressure values.

3. The blood pressure estimation method according to claim 1, wherein the calibration model is calculated using a partial least squares regression analysis method.

* * * * *